(12) United States Patent
Chen et al.

(10) Patent No.: US 11,000,535 B2
(45) Date of Patent: May 11, 2021

(54) ANTICANCER COMPOSITION AND USE THEREOF

(71) Applicant: KAOHSIUNG MEDICAL UNIVERSITY, Kaohsiung (TW)

(72) Inventors: Yi-Ming Chen, Kaohsiung (TW);
Chia-Hung Yen, Kaohsiung (TW);
Chung-Kuang Lu, Taipei (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 79 days.

(21) Appl. No.: 15/566,852

(22) PCT Filed: Apr. 14, 2016

(86) PCT No.: PCT/CN2016/079289
§ 371 (c)(1),
(2) Date: Mar. 2, 2018

(87) PCT Pub. No.: WO2016/165630
PCT Pub. Date: Oct. 20, 2016

(65) Prior Publication Data
US 2018/0214469 A1 Aug. 2, 2018

Related U.S. Application Data

(60) Provisional application No. 62/148,238, filed on Apr. 16, 2015.

(51) Int. Cl.
| | | |
|---|---|---|
| *A61K 31/7024* | (2006.01) | |
| *A23L 2/00* | (2006.01) | |
| *A61K 31/7034* | (2006.01) | |
| *A61K 45/06* | (2006.01) | |
| *A61P 35/00* | (2006.01) | |
| *A61K 31/44* | (2006.01) | |
| *A61K 36/22* | (2006.01) | |
| *A61K 36/65* | (2006.01) | |
| *G01N 33/50* | (2006.01) | |

(52) U.S. Cl.
CPC ............ *A61K 31/7024* (2013.01); *A23L 2/00* (2013.01); *A61K 31/44* (2013.01); *A61K 31/7034* (2013.01); *A61K 36/22* (2013.01); *A61K 36/65* (2013.01); *A61K 45/06* (2013.01); *A61P 35/00* (2018.01); *G01N 33/5011* (2013.01)

(58) Field of Classification Search
CPC .... A61K 31/7024; A61K 31/44; A61K 36/22; A61K 36/65; A61P 35/00; G01N 33/5011
USPC .......................................................... 514/25
See application file for complete search history.

(56) References Cited

FOREIGN PATENT DOCUMENTS

| CN | 103012510 A | * | 4/2013 |
| CN | 103520229 A |   | 1/2014 |

OTHER PUBLICATIONS

Li et al.; CN103012510 A; Apr. 3, 2013 (Machine-English Translation).*
Shen et al. (Zhongguo Yaoxue Zazhi (Beijing, China) (2013), 48(1), 22-24) (abstract sent).*
Bueno et al. (Fitoterapia (2014), 99, 252-260) (abstract sent).*
Duan et al.( Bioorganic & Medicinal Chemistry Letters 14 (2004) 6041 6044).*
Emam (Journal of Applied Sciences Research, 6(7): 888-896, 2010).*
Sun et al. (Arch. Pharm. Res. (2015) 38:1044-1053; Published online: Aug. 26, 2014).*
Djakpo et al. (Phytother. Res. 24: 1739-1747 (2010)).*
Song et al. (Shipin Kexue (Beijing, China) (2011), 32(19), 116-119) (abstract sent).*
Guo et al. (Zhongguo Yaofang (2013), 24(27), 2546-2548) (abstract sent).*
Kant, Rajni et al. "Identification of 1,2,3,4,6-Penta-O-galloyl-Dglucopyranoside as a Glycine N-Methyltransferase Enhancer by High-Throughput Screening of Natural Products Inhibits Hepatocellular Carcinoma". Int. J. Mol. Sci. 2016, 17, 669.
Kant, Rajni et al. "Supplementary Materials: Identification of 1,2,3,4,6-Penta-O-galloyl-Dglucopyranoside as a Glycine N-Methyltransferase Enhancer by High-Throughput Screening of Natural Products Inhibits Hepatocellular Carcinoma". Int. J. Mol. Sci. 2016, 17, 669.
Li, Huichen et al. "The Research Progress of Penta-O-Galloyl-B-D-Glucose in Anti-Tumour Effect", Journal of Modern Oncology, vol. 22, No. 9, Sep. 30, 2014 (Sep. 30, 2014), pp. 2255-2258, ISSN: 1672-4992.
Zhang, J.H. et al. "A simple statistical parameter for use in evaluation and validation of high throughput screening assays". J. Biomol. Screen. 1999, 4, 67-73.

* cited by examiner

*Primary Examiner* — Shaojia A Jiang
*Assistant Examiner* — Michael C Henry
(74) *Attorney, Agent, or Firm* — Volpe Koenig

(57) ABSTRACT

A composition for inhibiting a liver tumor in an organism is disclosed. The composition includes an activator being 1,2,3,4,6-penta-O-galloyl-Beta-D-glucopyranoside (PGG), wherein PGG is extracted from at least one of *Paeonia lactiflora* Pall. and Galla Chinesis.

1 Claim, 28 Drawing Sheets
Specification includes a Sequence Listing.

Days after the treatment

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: CBE upstream linker

<400> SEQUENCE: 1
cgatatcgga tccgtcgacg                                                     20

<210> SEQ ID NO 2
<211> LENGTH: 22
<212> TYPE: DNA
<213> ORGANISM: Artificial Sequence
<220> FEATURE:
<223> OTHER INFORMATION: CBE downstream linker

<400> SEQUENCE: 2
aattcgtcga cggatccgat at                                                  22

<210> SEQ ID NO 3
<211> LENGTH: 19
<212> TYPE: DNA
<213> ORGANISM: Artificial Sequence
<220> FEATURE:
<223> OTHER INFORMATION: GNMT upstream primer

<400> SEQUENCE: 3
actggatgac tctggacaa                                                      19

<210> SEQ ID NO 4
<211> LENGTH: 17
<212> TYPE: DNA
<213> ORGANISM: Artificial Sequence
<220> FEATURE:
<223> OTHER INFORMATION: GNMT downstream primer

<400> SEQUENCE: 4
actgaggatg tggtcgt                                                        17
```

```
<210> SEQ ID NO 5
<211> LENGTH: 21
<212> TYPE: DNA
<213> ORGANISM: Artificial Sequence
<220> FEATURE:
<223> OTHER INFORMATION: TBP upstream primer

<400> SEQUENCE: 5
tgcacaggag ccaagagtga a                                        21

<210> SEQ ID NO 6
<211> LENGTH: 20
<212> TYPE: DNA
<213> ORGANISM: Artificial Sequence
<220> FEATURE:
<223> OTHER INFORMATION: TBP downstream primer

<400> SEQUENCE: 6
cacatcacag ctcccacca                                           20

<210> SEQ ID NO 7
<211> LENGTH: 22
<212> TYPE: DNA
<213> ORGANISM: Artificial Sequence
<220> FEATURE:
<223> OTHER INFORMATION: c-Myc upstream primer

<400> SEQUENCE: 7
ttcggttgtt gctgatctgt ct                                       22

<210> SEQ ID NO 8
<211> LENGTH: 21
<212> TYPE: DNA
<213> ORGANISM: Artificial Sequence
<220> FEATURE:
<223> OTHER INFORMATION: c-Myc downstream primer

<400> SEQUENCE: 8
ccctccactc ggaaggacta t                                        21
```

ANTICANCER COMPOSITION AND USE THEREOF

CROSS-REFERENCE TO RELATED APPLICATION AND CLAIM OF PRIORITY

The application is a National Stage Entry of International Patent Application No. PCT/CN2016/079289, filed on Apr. 14, 2016, at the World Intellectual Property Office, and claims priority to U.S. Provisional Patent Application No. 62/148,238, filed on Apr. 16, 2015, the disclosures of which are incorporated herein in their entirety by reference.

FIELD OF THE INVENTION

The present invention discloses a composition and a use for anti-cancer, and more particularly it is related to a bioactivity treatment with 1,2,3,4,6-penta-O-galloyl-Beta-D-gluco-pyranoside (PGG) or the composition combined with a sorafenib.

BACKGROUND OF THE INVENTION

Globally, hepatocellular carcinoma (HCC) is a very common cancer currently ranking third in mortality. More than five million new cases are diagnosed globally every year. The morbidity rate is almost equal to the mortality rate due to unclear diagnosis, imperfect treatment and a high recurrence rate for HCC.

Glycine N-methyl transferase (GNMT) has a plurality of bioactivite functions, one of which is as a tumor suppressor gene for hepatocellular carcinomas (HCC).

GNMT prevents aflatoxin-induced and polyaromatic hydrocarbons-induced carcinogenicity and inhibits liver cancer cell proliferation by reducing DNA adduct formation and cytotoxicity.

Some studies have shown that GNMT is involved in the onset of hepatic detoxification pathways. It was also found that the expression of GNMT decreases in more than 80% of HCC patients, in which the risk to become cirrhosis patients increases. In addition, high rates of both genders of GNMT knockout mice developed HCC spontaneously.

However, transgenic mice with human GNMT overexpression in their livers resisted aflatoxin $B_1$-induced liver tumorigenesis. Moreover, recent studies have shown that overexpression of GNMT inhibits cancer cell proliferation.

To date, only sorafenib (trade name Nexavar) has been approved for the treatment of HCC in America. However, it has side effects, and patients quickly develop resistance to it. Therefore, there is an unmet need for more effective drugs for HCC.

In the meanwhile, natural products have been regarded as an unlimited resource for novel drug discovery. It has been estimated that up to 1990, nearly 80% of drugs were either natural products or their analogs.

Among natural products, traditional Chinese medicine has a unique position, since it represents a wide diversity of plants that has been used by human beings for a long period of time.

In order to overcome the drawbacks in the prior art, a composition for anti-cancer and use thereof are disclosed. The particular design in the present invention not only solves the problems described above, but also is easy to implement. Thus, the present invention has utility for the industry.

SUMMARY OF THE INVENTION

The objects of the present invention are to provide a combination of multiple modes of administration, and to seek various uses of pharmaceuticals and foods.

In accordance with one aspect of the present invention, a composition for inhibiting a liver tumor in an organism is disclosed. The composition comprises: an activator being 1,2,3,4,6-penta-O-galloyl-Beta-D-glucopyranoside (PGG), wherein PGG is extracted from at least one of *Paeonia lactiflora* Pall. and Galla Chinesis.

In accordance with another aspect of the present invention, a method of manufacturing a pharmaceutical composition for a treatment of a liver cancer is disclosed, in which the pharmaceutical composition comprising a compound of 1,2,3,4,6-penta-O-galloyl-Beta-D-glucopyranoside (PGG).

In accordance with another aspect of the present invention, a method for evaluating a therapeutic effect of a medicament in treating a liver tumor is disclosed. The method comprises the steps of: (a) providing a Huh7 Glycine N-methyltransferase (GNMT) promoter-luciferase (H7GPL) cell model for the liver tumor; (b) administering to the Huh7 Glycine N-methyltransferase (GNMT) promoter-luciferase (H7GPL) cell model the medicament to be tested for the therapeutic effect; and (c) determining whether the medicament is effective for treating the liver tumor based on a GNMT promoter-driven luciferase reporter assay.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

Figure 1:
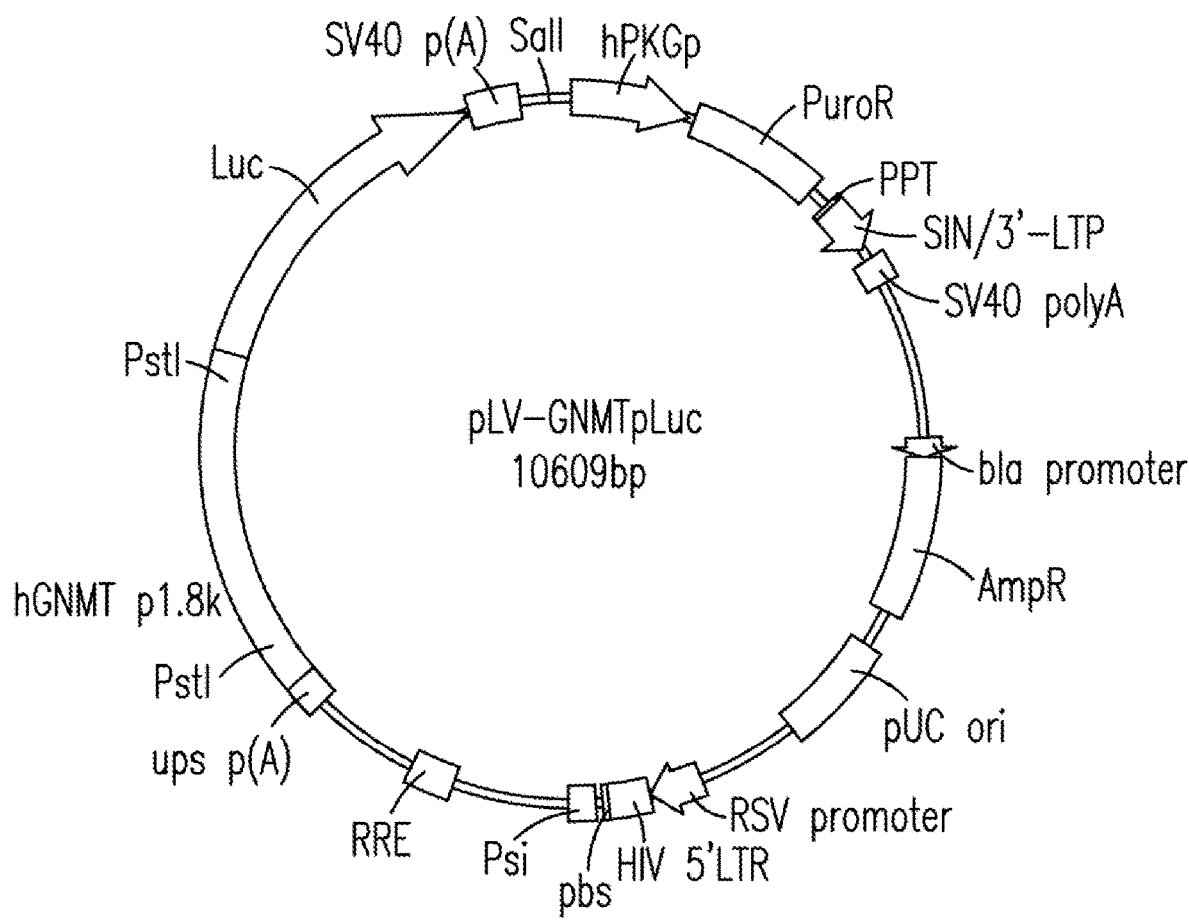
FIG. 1 illustrates the configuration of pLV-GNMTpLuc plasmid.

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

The terms "treating", "treatment" and the like are referred to a method to alleviate, improve, reduce or eliminate disorders from which a patient is suffering or any symptoms associated with the disorders, and a method relating to preventing associated conditions or symptoms.

The term "a therapeutically effective amount" is referred to a dose sufficient to ameliorate or prevent medical symptoms or physiological state being worser. Also an effective dose is referred to administration at a dose sufficient for diagnosis.

Unless there is a description in the specification, "the active compound" and "pharmaceutically active compound" can be used interchangeably herein, referring to a substance capable of pharmaceutical, pharmacological or therapeutic effects.

The term excipients or "pharmaceutically acceptable carriers or excipients" and "bio-available carriers or excipients" mentioned above include any appropriate compounds known to be used for preparing the dosage form, such as a solvent, dispersing agent, coating, anti-bacterial or anti-fungal agent, preservation agents or a delayed absorbent.

Typically, such a carrier or excipient does not itself have therapeutic activity. Each formulation prepared by combining the derivatives disclosed in the present invention and the pharmaceutically acceptable carriers or excipients will not cause any undesired effects, allergy or other inappropriate effects when being administered to an animal or human. Accordingly, the derivatives disclosed in the present invention in combination with the pharmaceutically acceptable carrier or excipients are adaptable for clinical usage and in humans.

The term excipients or "pharmaceutically acceptable carriers or excipients" and "bio-available carriers or excipients" mentioned above include any appropriate compounds known to be used for preparing the dosage form, such as a solvent, dispersing agent, coating, anti-bacterial or anti-fungal agent, preservation agents or a delayed absorbent.

The term "pharmaceutical composition" or "medicament" is referred to a liquid or solid composition with a proper form, concentration and degree of purity suitable for administration to a subject (e.g., human or animal). After administration, a desired physiological response can be induced. Pharmaceutical compositions are typically sterile and/or non-pyrogenic.

In some embodiments, combination therapies are referred to patients administering an oral composition containing 1,2,3,4,6-pentagalloyl-D-glucose (PGG) in a single dose, such as tablets, capsules or foods containing containing PGG.

Or a combination therapy by administering a different formulation or the same one containing sorafenib is taken. Where separate dosage formulations of different active agent are used, they can be administered in another administration type at essentially the same time or separated by a period of time.

An example of combination treatment may be by any suitable administration route including oral (including buccal and sublingual), rectal, nasal, vaginal, and parenteral (including subcutaneous, intramuscular, intravenous and intradermal).

Topical administrations include, but are not limited to, sprays, plaster, mist, aerosols, solutions, lotions, gels, creams, ointments, pastes, unguents, emulsions and suspensions, with oral or parenteral being preferred. The period of time during administration is often referred to within three hours.

[Establishment of a GNMT Expression Oriented Cell-Based Drug Screening Platform]

After cloning Glycine N-methyl-transferase (GNMT) promoter region, the firefly luciferase (LUC) reporter gene is transfected into lentiviral vector-pLKO.1.

Please refer to FIG. 1, which illustrates the configuration of pLV-GNMTpLuc plasmid. HEK293T cells were cotransfected with a packaging plasmid-pCMV-ΔR8.91, a VSV-G envelope expressing plasmid-pMD.G and pLV-GNMTpLuc using TurboFect™ Reagent (Fermentas, Hanover, Md.). One resultant colony was picked, amplified and denominated as H7GPL (HuH-7-GNMT promoter-Luciferase). The relative luciferase activity (RLA) was calculated as "activity of luciferase/intensity of alamarBlue fluorescence". The fold changes in GNMT promoter induction was calculated as "RLA of drug/RLA of solvent control". Compounds with the ability to activate human glycine N-methyltransferase promoter in H7GPL could serve as a citeria for screening drugs.

Figure 2:
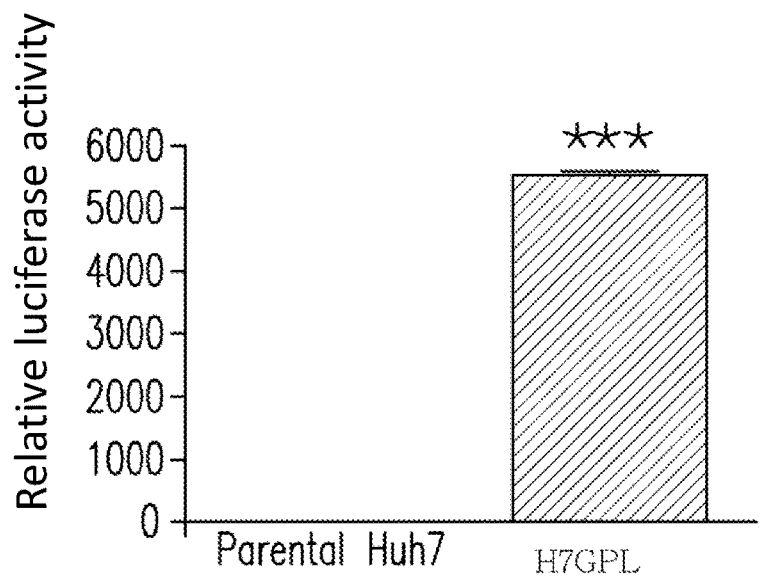
FIG. 2 illustrates the luciferase activity in a screening platform.

Please refer to FIG. 2, which illustrates the luciferase activity in a screening platform. Previously, 26 FDA approved drugs were identified that can reverse the gene expression signature of HCC. We obtained 26 drugs. H7GPL cells were seeded in 96-well plates for 18 hours and then were treated with these 26 drugs and solvent control for an extra 24 hours. It was found that 6 out of these 26 drugs can enhance GNMT promoter activity.

Small molecule drugs in Table 1 having the potential to treat liver cancer can affect the GNMT promoter activity.

TABLE 1

| No. | Drug Name | Catalog no. | Fold change (10 uM) |
|---|---|---|---|
| 1 | Tanespimycin (galadenamycin) | A8476 | 0.5 |
| 2 | Camptothecin | C9911 | 0.4 |
| 3 | Pyrvinium | P0027 | 0.5 |
| 4 | Sanguinarine | S5890 | 0.1 |
| 5 | withaferin A | W4394 | 0 |
| 6 | Mefloquine | M2319 | 0.3 |
| 7 | Mebendazole | M2523 | 1 |
| 8 | Chlorpromazine | C8138 | 0.7 |
| 9 | Sulconazole | S9632 | 0.5 |
| 10 | Bepridil | B5016 | 0.7 |
| 11 | Ciclopirox | C0415 | 8.2 |
| 12 | clioquinol(quinoinol) | 24880 | 3.8 |
| 13 | GW-8510 | G7791 | 0.4 |
| 14 | Prochlorperazine | P9178 | 0.7 |
| 15 | Thioridazine | T9025 | 0.1 |
| 16 | Tyloxapol | T0307 | 0.6 |
| 17 | Apigenin | 10798 | 1.8 |
| 18 | Cloperastine | C2040 | 1 |
| 19 | Dipyridamole | D9766 | 0.9 |
| 20 | Luteolin | L9283 | 1.9 |
| 21 | Phenoxybenzamine | B019 | 0.7 |
| 22 | DO 897/99 | B9308 | 0.9 |
| 23 | Trifluoperazine | T8516 | 0.1 |
| 24 | Trioxysalen | T6137 | 1.2 |
| 25 | suberoylanilide hydroxamic acid | S1047 | 18.6 |
| 26 | trichostatin A | T8552 | 3.4 with Fold change (0.2 uM) |

As shown in Table 1, ciclopirox, Clioquinol, apigenin, luteolin, suberoylanilide hydroxamic acid, trichostatin A as well as trichostatin A (TSA) selected from 26 drugs remarkably induced GNMT promoter activity. Therefore, we established and evaluated a GNMT promoter-driven drug screening assay as a valuable platform for high throughput screening of compounds for the treatment of HCC.

Suberoylanilide hydroxamic acid (SAHA) was shown to be a potent GNMT inducer. We further evaluated the qualification of H7GPL cells as a drug screening platform with SAHA.

Figure 3:
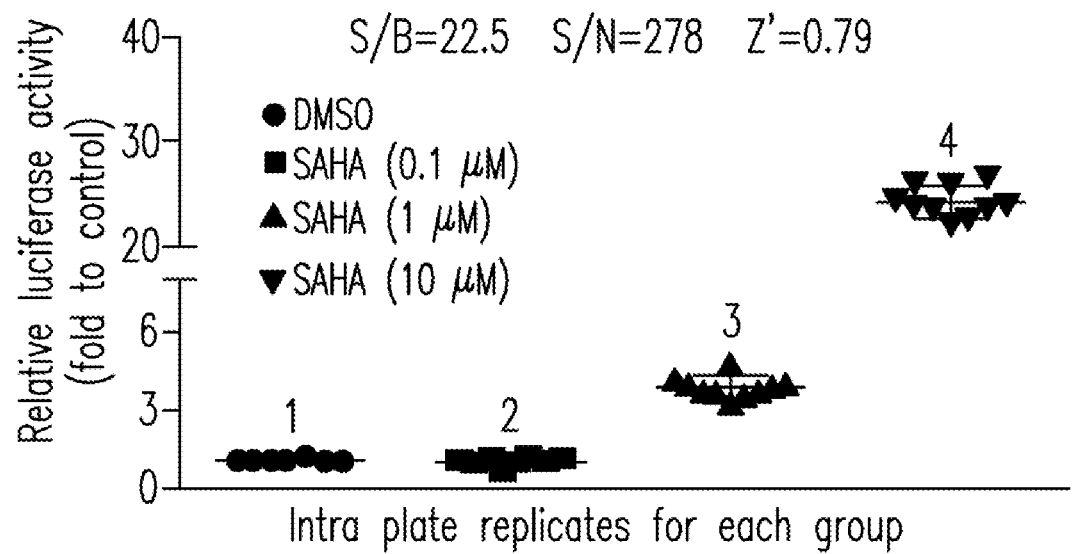
FIG. 3 illustrates the reaction of different drugs in the screening platform.

Please refer to FIG. 3, which shows the reaction of different drugs in the screening platform. H7GPL cells responded to SAHA dose-dependently and showed a small inter-well variation. That Assay quality is typically determined according to the Z' factor (Zhang, J. H.; Chung, T. D.; Oldenburg, K. R. *A simple statistical parameter for use in evaluation and validation of high throughput screening assays*. J. Biomol. Screen. 1999, 4, 67-73). To determine the quality of the platform for drug screening, the promoter activities were used to calculate the statistical parameters, such as the signal-to-background (SB) ratio, the signal-to-noise (S/N) ratio and the value of the Z' factor.

[Screening a Traditional Chinese Medicine Drug Library]

We screened a library containing 324 pure compounds and 480 crude extracts prepared from traditional Chinese medicine and herbs which were provided by National Research Institute of Chinese Medicine (NRICM).

In the initial screening, when (individual luciferase activity−average luciferase activity of all hits)/standardized Z scores of all samples is greater than 1.5, it means the compound has the capability of enhancing the GNMT reporter activity.

Figure 4:
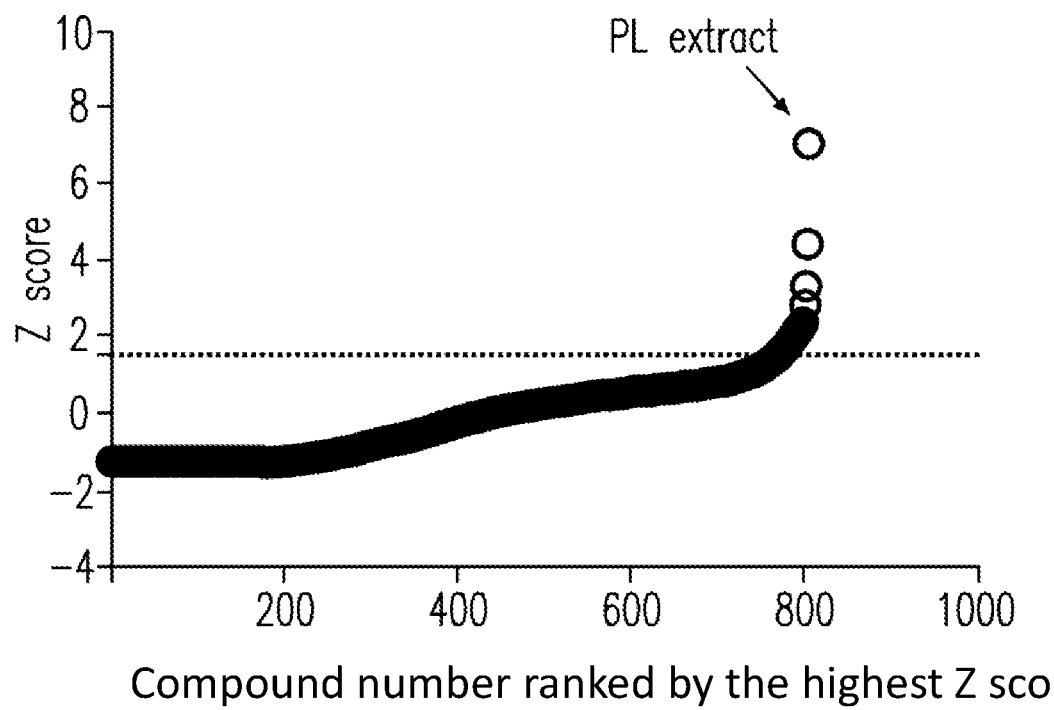
FIG. 4 illustrates a screening from a drug library.

Please refer to FIG. 4, which illustrates a screening from a drug library. There were 26 hits (13 pure compounds and 13 herb extracts) obtained with Z scores of greater than 1.5.

[The Anti-HCC Effect of *Paeonia lactiflora* Pall. Extract Derived Bioactive Fraction]

Figure 5:
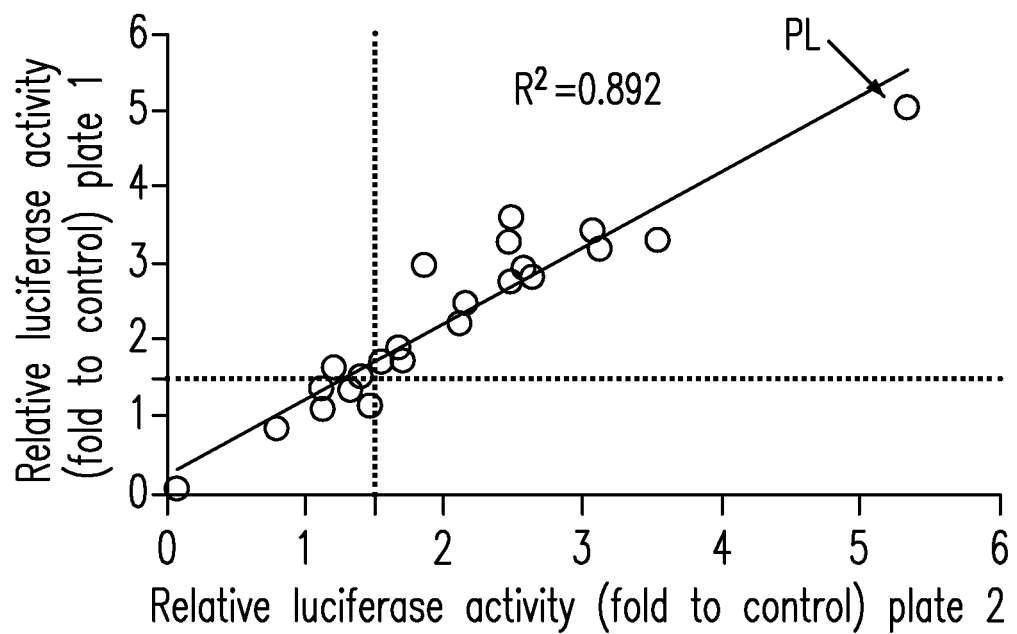
FIG. 5 illustrates that *Paeonia lactiflora* Pall. (PL) extract has the most significant luciferase activity.

Please refer to FIG. 5, which illustrates the *Paeonia lactiflora* Pall. (PL) extract has the most significant luciferase activity.

Figure 6:
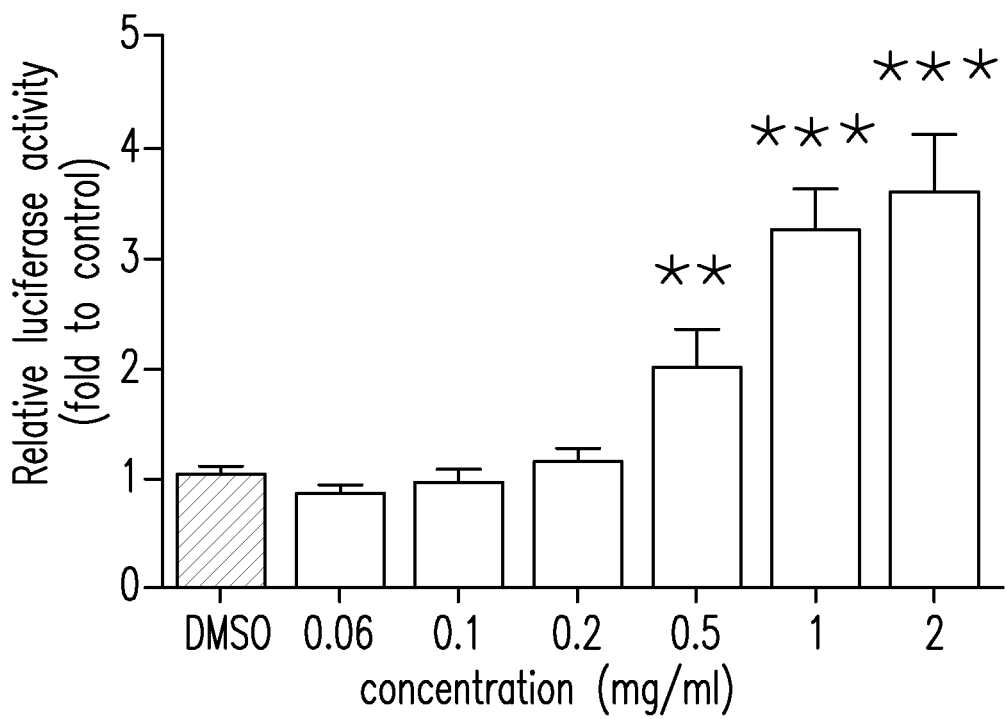
FIG. 6 illustrates the relationship between the activity and the dose in *Paeonia lactiflora* Pall.
Figure 7:
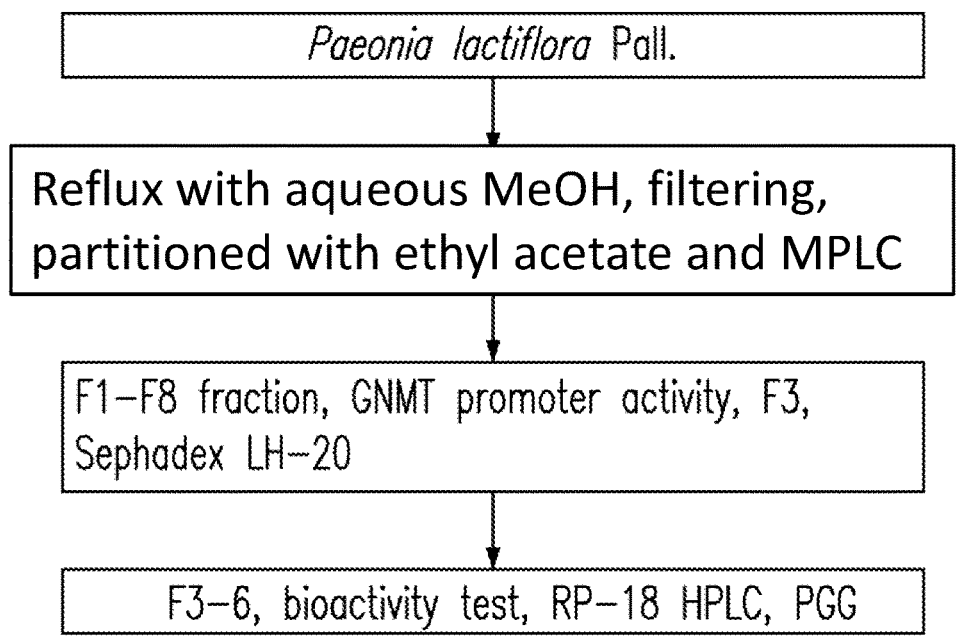
FIG. 7 shows Scheme 1.

We identified the extract of *Paeonia lactiflora* Pall (PL) as the highest inducer of GNMT promoter activity. We further confirmed that PL extract increases GNMT promoter activity in a dose-dependent manner as illustrated in FIG. 6 and FIG. 7.

[Identification of Active Subfraction of *Paeonia lactiflora* Pall. Extracted by Bioassay Guided Fractionation]

To identify the active compounds in PL extract that contributed to the GNMT driven luciferase activity, ethanol extract from PL was further fractionated and purified in eight different fractions and then tested for GNMT promoter activity.

Figure 8:
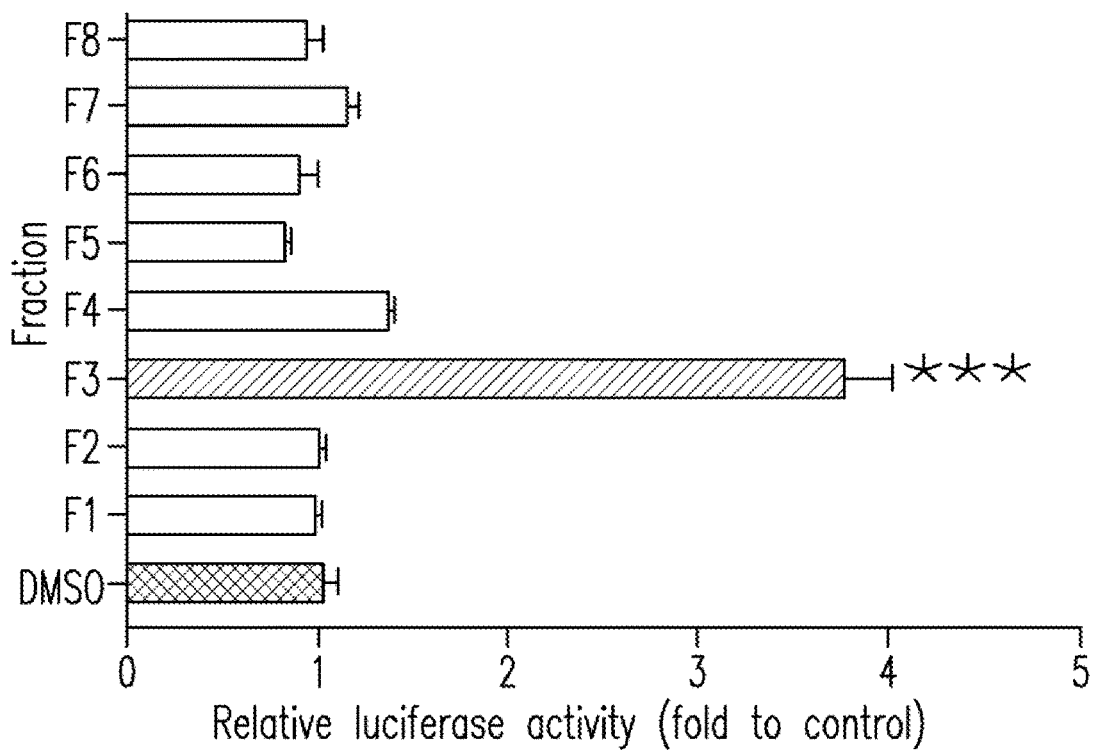
FIG. 8 illustrates the activities in fractions F1-F8.

Please refer to FIG. 8, which illustrates the activities in fractions F1-F8 and tests for GNMT promoter activity. The Fraction F3 showed most potent induction of GNMT promoter activity was used for further isolation and purification.

Figure 9:
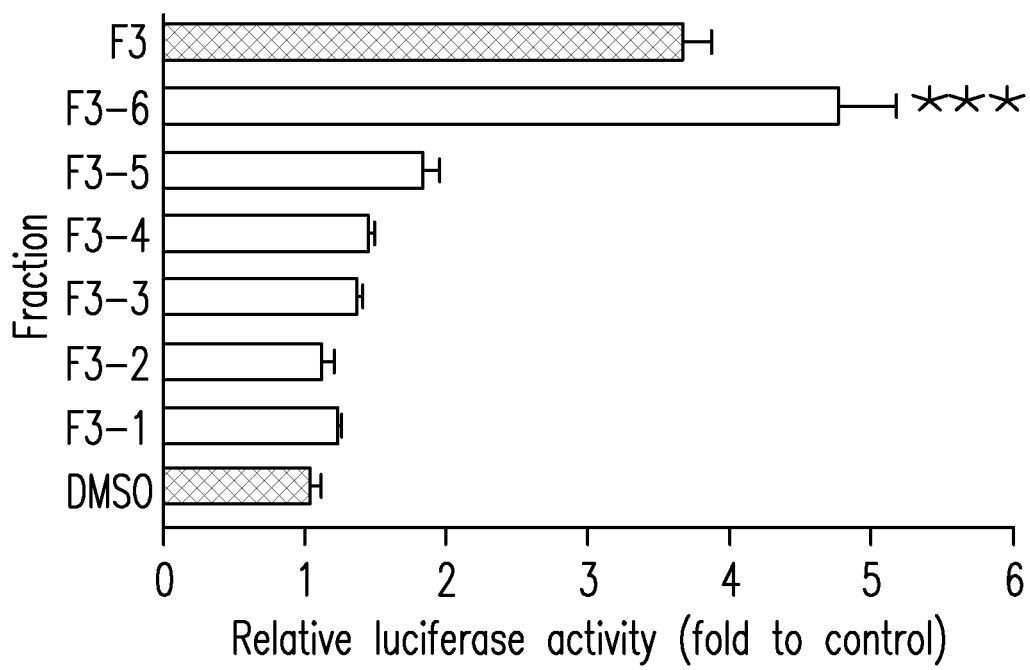
FIG. 9 illustrates the activities in fractions F3, F3-1 to F3-6.

Please refer to FIG. 9, which illustrates the activities in fractions F3, F3-1 to F3-6. Further purification of the most active fraction (F3) was performed on a Sephadex LH-20 column using MeOH as the mobile phase and obtained the bioactive fraction of F3-6 with the ability by changes in more than 4 folds.

Figure 10:
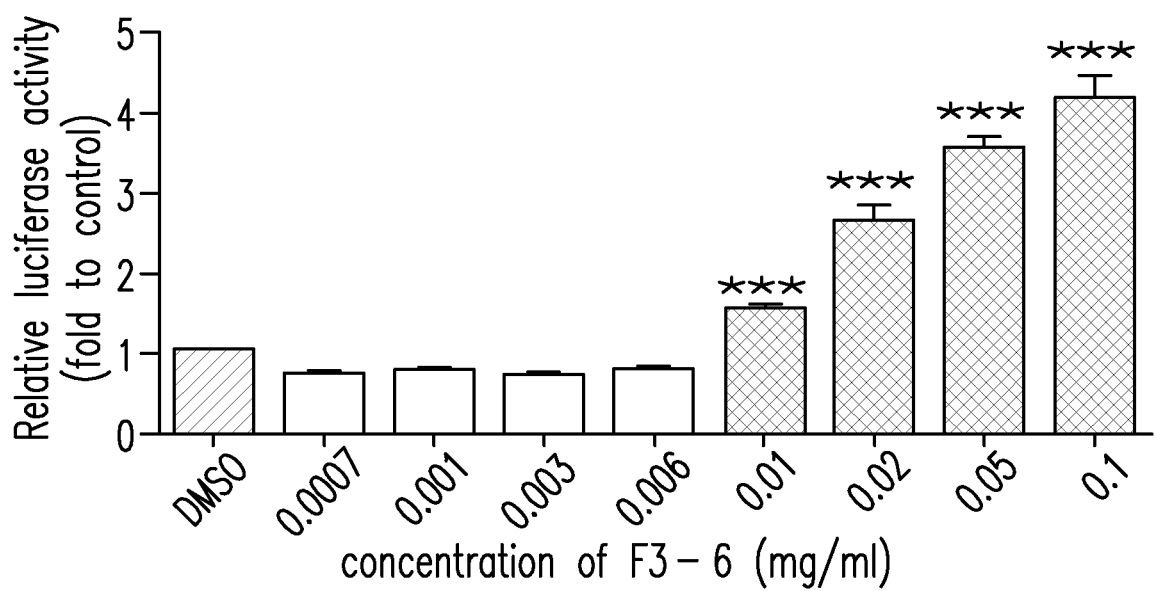
FIG. 10 illustrates the dose-dependent mode for activities in fraction F3-6.

Please refer to FIG. 10, which illustrates the dose-dependent mode for activities in the fraction F3-6.

Figure 11A:
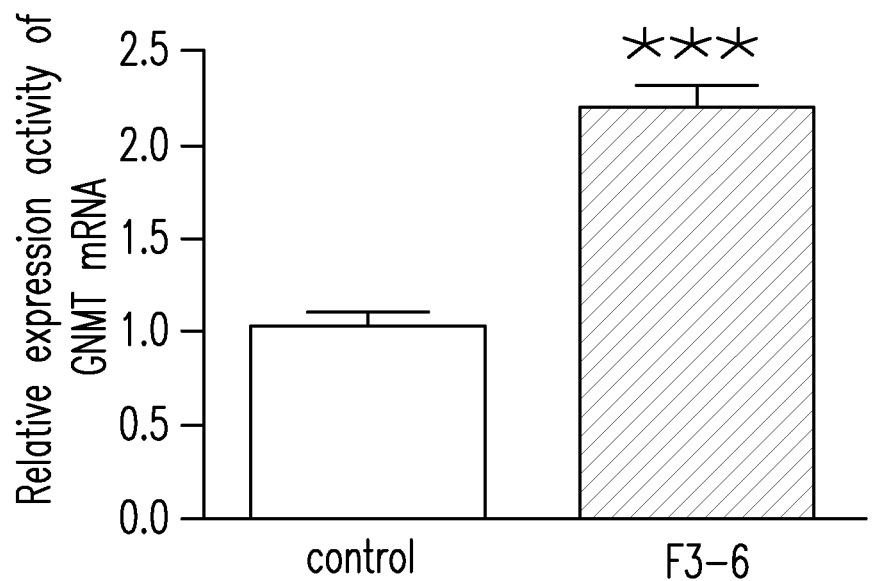
FIG. 11A illustrates the relative expression activity of GNMT mRNA in Huh7 cells.
Figure 11B:
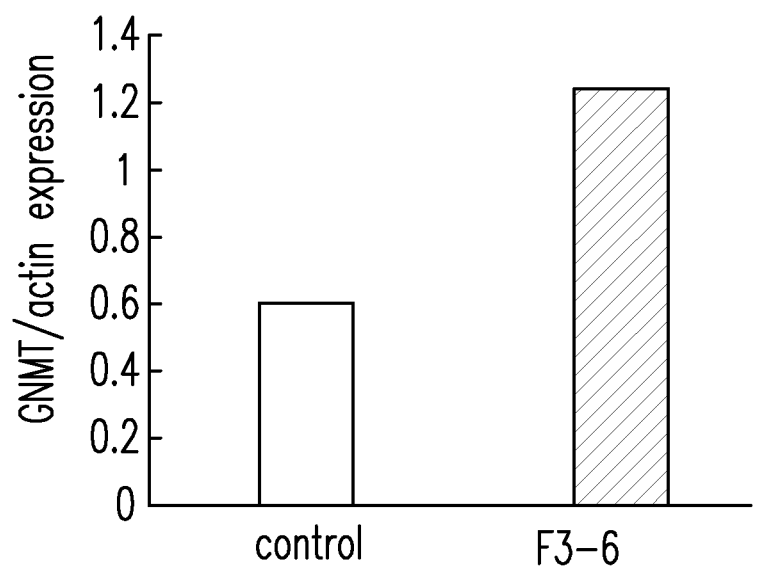
FIG. 11B illustrates the GNMT protein expression in Huh7 cells.

Please refer to FIG. 11A, which illustrates the relative expression activity of GNMT mRNA in Huh7 cells; and FIG. 11B illustrates the GNMT protein expression in Huh7 cells.

Figure 12:
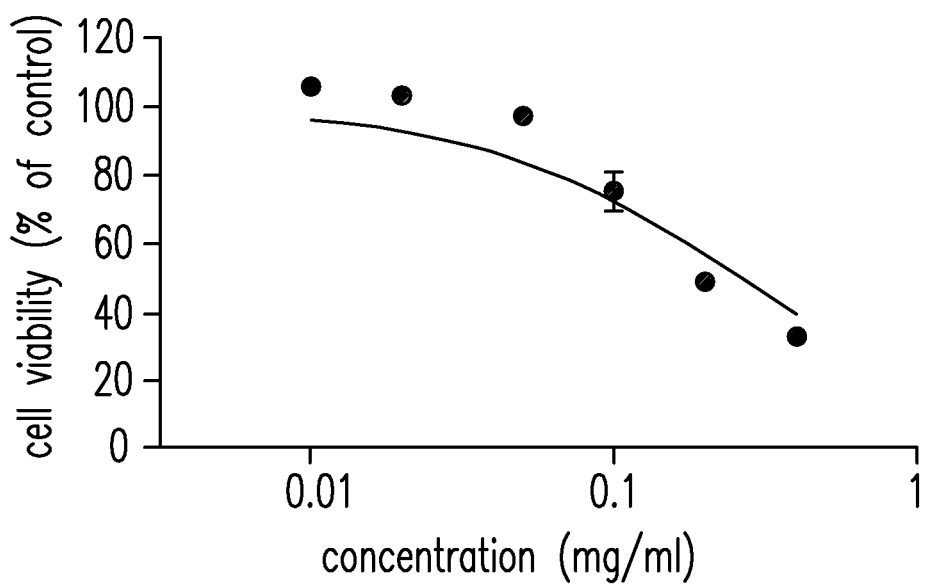
FIG. 12 illustrates fraction F3-6 inhibits the proliferation in Huh7 cells.

Please refer to FIG. 12, which illustrates the fraction F3-6 inhibit the proliferation in Huh7 cells.

Figure 13:
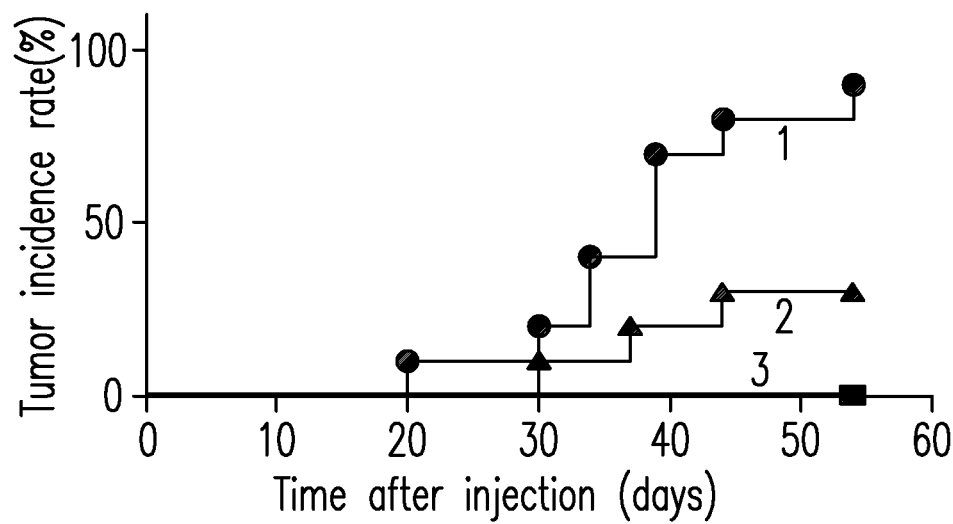
FIG. 13 illustrates tumor incidence rate in percentages, wherein numeral 1 denotes vehicle control; numeral 2 denotes 25 mpk and numeral 3 denotes is 300 mpk.

Please refer to FIG. 13 which illustrates tumor incidence rate in percentages. In vivo xenograft studies in NOD-SCID mice showed that the incidence of tumor formation in PR_E2_PF6 treated mice was significantly lower than solvent treated mice injected with Huh7 cells. After 20 days of cell inoculation, control group mice began to develop tumors. In vivo xenograft studies in NOD-SCID mice showed that the incidence of tumor formation in PR_E2_PF6 treated mice was significantly lower than in solvent treated mice injected with Huh7 cells. Furthermore, 80% of mice developed tumors in solvent group; however none of the mice in PR_E2_PF6 (300 mpk) and only 33% of mice in PR_E2_PF6 (25 mpk) group had visible tumors after 52 days of cell inoculation.

Figure 14:
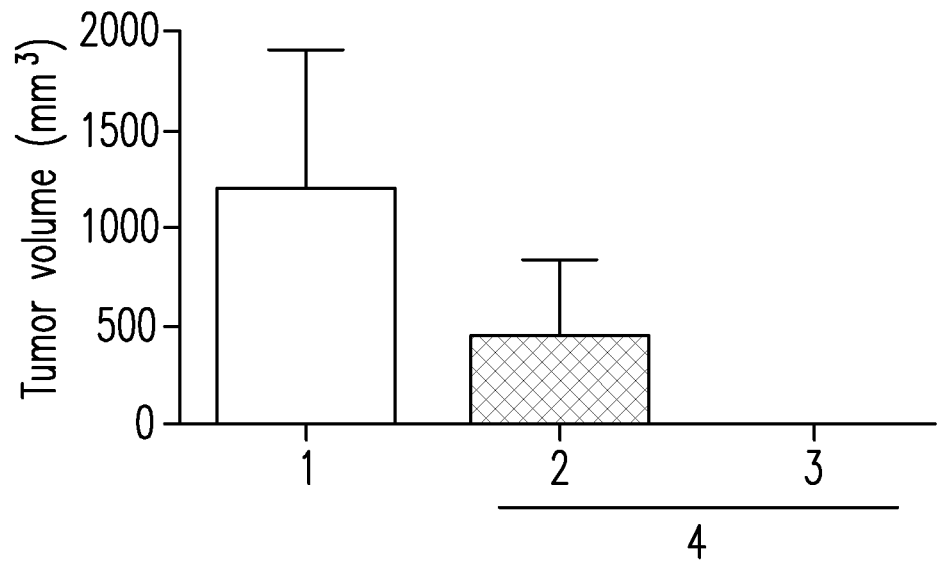
FIG. 14 illustrates the relationship between the tumor volume and dose, wherein numeral 1 denotes solvent, numeral 2 denotes 25 mpk, numeral 3 denotes 300 mpk, and numeral 4 denotes F3-6.

Please refer to FIG. 14, which illustrates the relationship between the tumor volume and dose. Moreover reduced tumor growth was observed in the PR_E2_PF6 treatment group compared with control group.

[PGG, the Active Component in F3-6, Inhibits Liver Cancer Cells Growth Both In Vitro and In Vivo]

Figure 15:
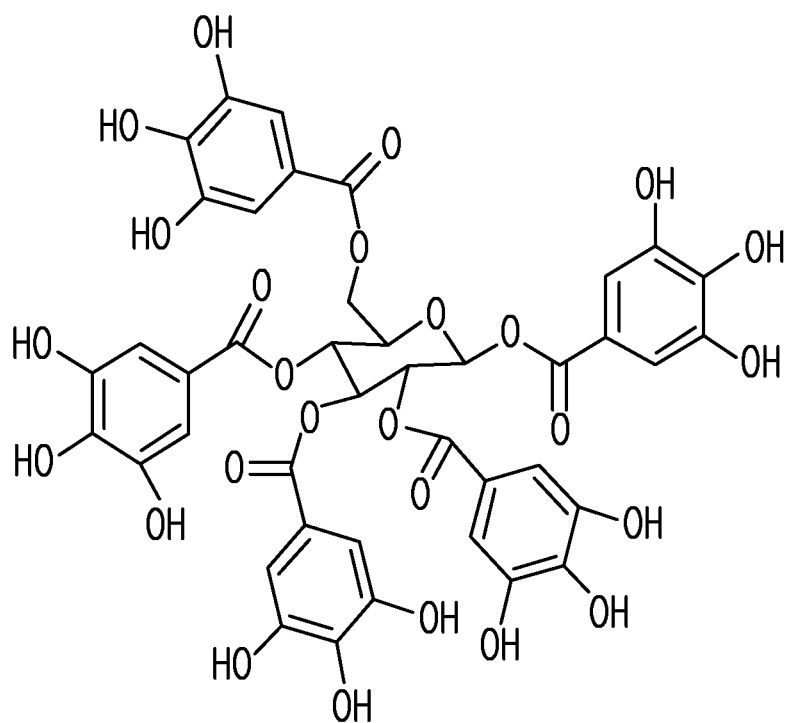
FIG. 15 illustrates structural formula of 1,2,3,4,6-penta-O-galloyl-Beta-D-gluco-pyranoside (PGG)

Please refer to FIG. 15, which illustrates structural formula of 1,2,3,4,6-penta-O-galloyl-Beta-D-gluco-pyranoside (PGG). The F3-6 fraction was further purified by HPLC, and 1,2,3,4,6-penta-O-galloyl-β-D-glucopyranoside (PGG, purity >98%) was identified as the active component in the fraction F3-6.

Figure 16:
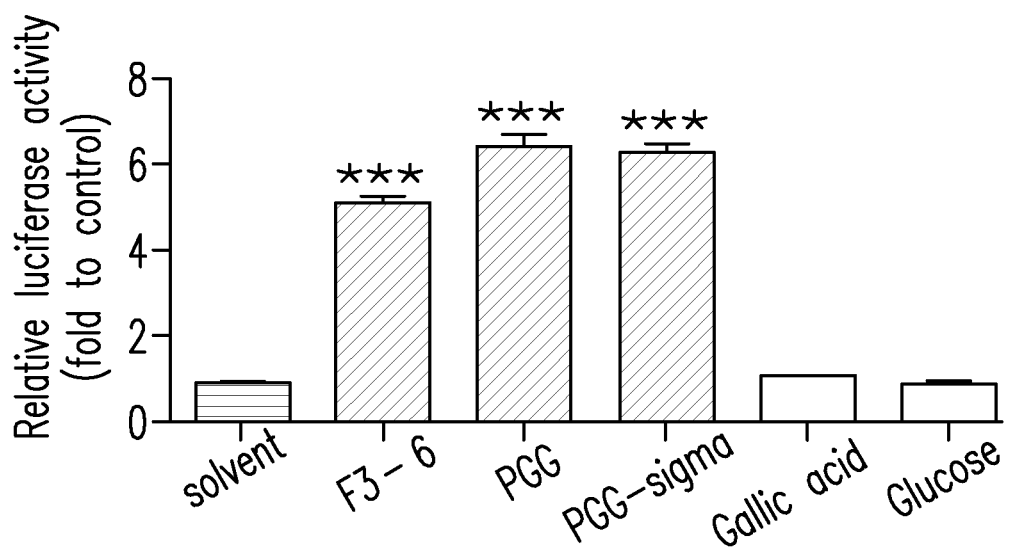
FIG. 16 illustrates the dose-dependent mode for activities in the fraction F3-6.

Please refer to FIG. 16, which illustrates the dose-dependent mode for activities in the fractions F3-6. PGG either purified from F3-6 or purchased from Sigma can induce GNMT promoter activity.

Although the structure of 1,2,3,4,6-pentagalloyl-D-glucose is composed of a glucose group and a gallic acid group, none of which can either affect the activity of GNMT promoter or induce the the activity of GNMT promoter.

Figure 17A:
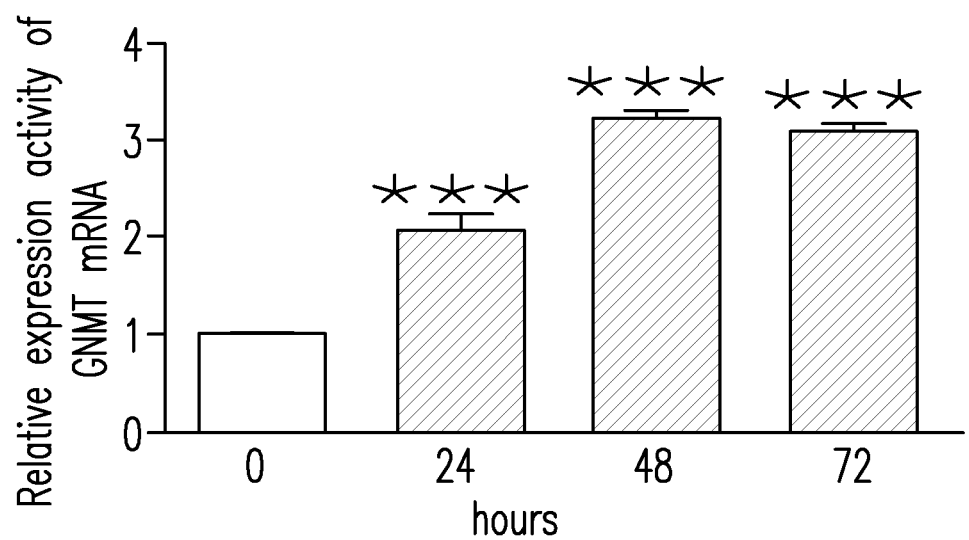
FIG. 17A illustrates PGG (0.1 mg/ml) induced GNMT mRNA expression in Huh7 cells.
Figure 17B:
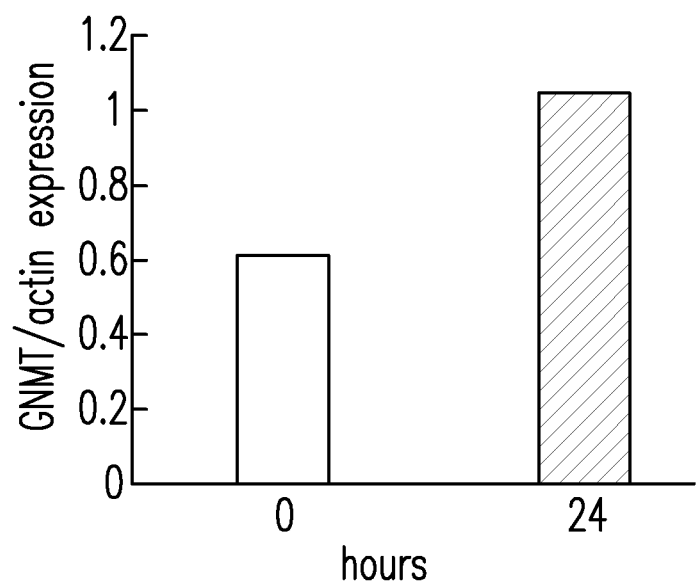
FIG. 17B illustrates PGG (0.1 mg/ml) induced GNMT protein expression in Huh7 cells.

Please refer to FIG. 17A, which illustrates PGG (0.1 mg/ml) induced GNMT mRNA expression in Huh7 cells. Please refer to FIG. 17B, which illustrates PGG (0.1 mg/ml) induced GNMT protein expression in Huh7 cells. Finally, qPCR and immunoblot analysis of tumor samples revealed that GNMT was induced in the PGG-treated group in a time-dependent manner, and then it has the optimal induced effect at 48 hours after administration.

Next, we analyzed the effect of PGG on cell proliferation in different liver cancer cell lines, including Huh7, Hep3B (ATCC-No 8064), HepG2 (ATCC HB-8065), SK-HEP-1 (ATCC HTB-52), Mahlavu and HepG2 (ATCC HB-8065).

Figure 18:
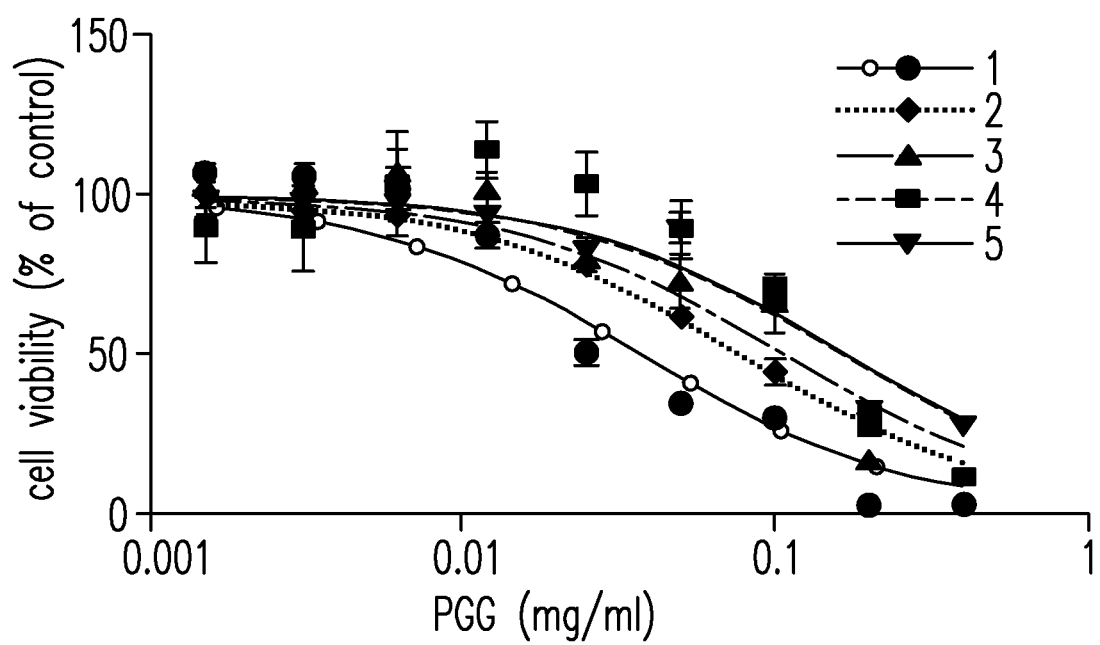
FIG. 18 illustrates the effect of PGG on cell proliferation in different liver cancer cell lines, wherein the numeral 1 denotes Huh7 cells, the numeral 2 denotes Hep3B cells, the numeral 3 denotes SK-HEP-1 cells, the numeral 4 denotes Mahlavu cells and the numeral 5 denotes HepG2 cells.

Please refer to FIG. 18, which illustrates the effect of PGG on cell proliferation in different liver cancer cell lines, wherein the numeral 1 denotes Huh7 cells, the numeral 2 denotes Hep3B cells, the numeral 3 denotes SK-HEP-1 cells, the numeral 4 denotes Mahlavu cells, and the numeral 5 denotes HepG2 cells. And cell viability was determined by the alamarBlue® viability assay. $IC_{50}$ values of PGG in each cell line are shown as follows: Huh7 cells 0.03 mg/mL, Hep3B cells 0.07 mg/mL, SK-HEP-1 cells, Mahlavu cells and HepG2 0.10 mg/mL dose-dependent.

For the colony assay, Huh7 cells were seeded. After an overnight incubation, cells were treated with drugs at the specified concentrations for 7 days. Numbers of surviving colonies were analyzed.

Figure 19:
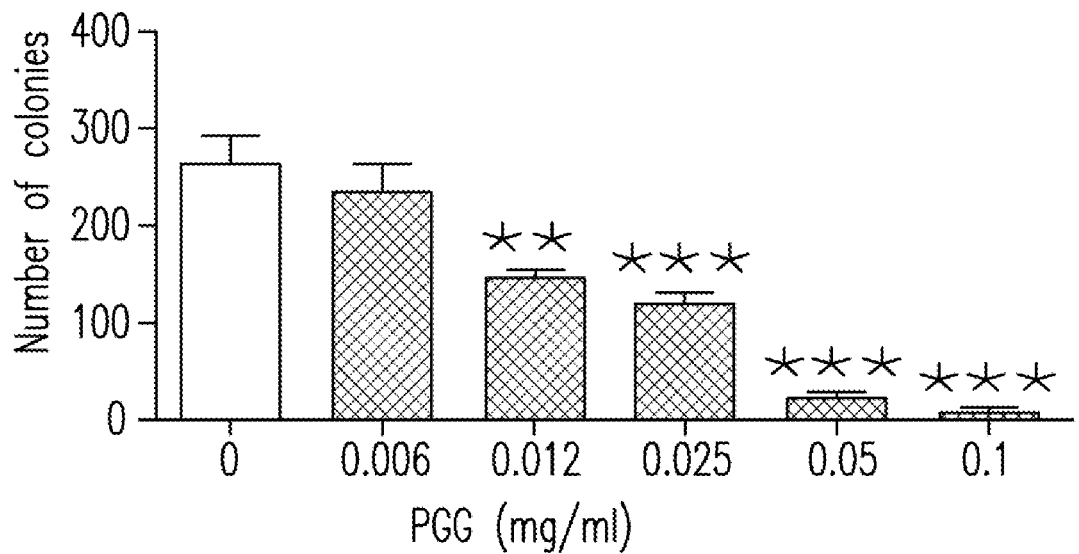
FIG. 19 illustrates the colony formation of Huh7 cells.

Please refer to FIG. 19, which illustrates the colony formation of Huh7 cells. PGG can reduce the formation of Huh7 cell populations in a dose-dependent manner. As shown in FIG. 19, the inhibition at a concentration of 0.05 mg/ml or higher reaches 95%.

To test the antitumor effect of PGG in vivo, Huh7 cells were implanted subcutaneously into nude mice. When the tumors of nude mice are detected in a significantly growing status, the nude mice are randomly divided into two groups with respective treatments: a vehicle and PGG (300 mpk) for 10 days.

Figure 20:
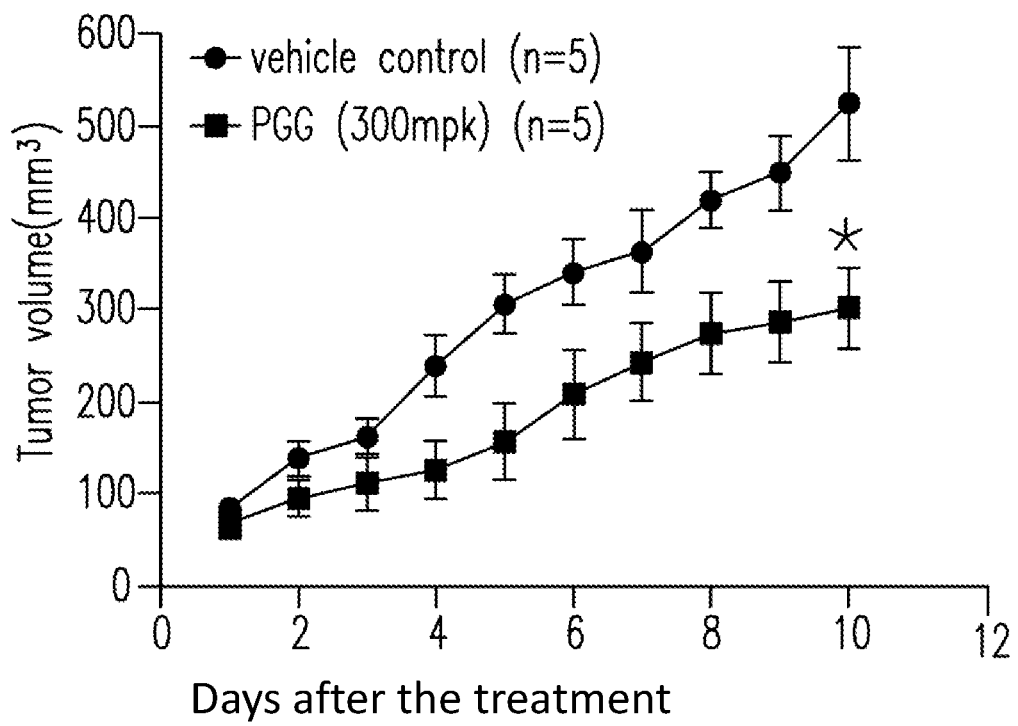
FIG. 20 illustrates the tumor volume after the treatment.

Please refer to FIG. 20, which illustrates the tumor volume after the treatment. Compared with the control group, there is a significant inhibition in tumor growth in the group treating with PGG (300 mpk) as shown in FIG. 20.

Figure 21:
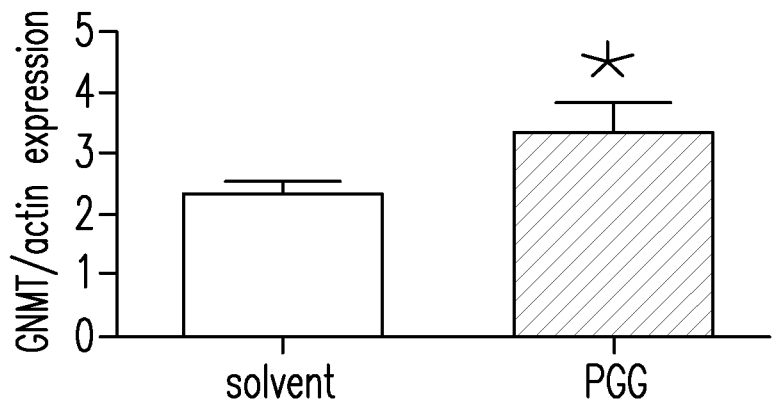
FIG. 21 illustrates GNMT/actin expression in the tumor tissue.

Please refer to FIG. 21, which illustrates GNMT/actin expression in the tumor tissue. Immunoblot analysis of tumor samples revealed that GNMT was induced in the PGG-treated group as illustrated in FIG. 21.

[PGG Treatment Induces Apoptosis in Huh7 Cells]

Figure 22:
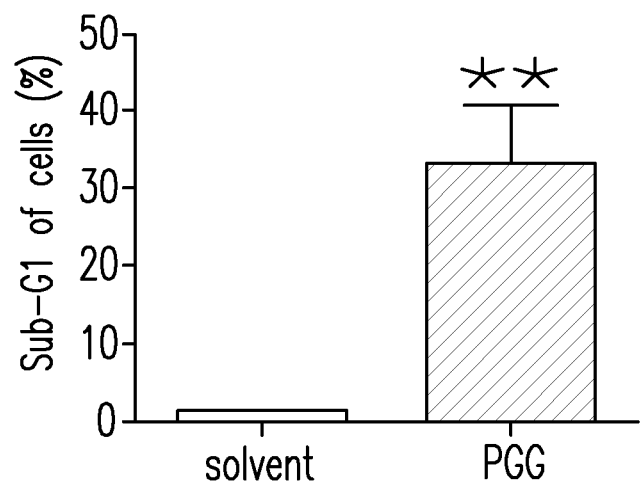
FIG. 22 illustrates sub-G1 of cells in population.

Please refer to FIG. 22, which illustrates sub-G1 of cells in population. And flow cytometry analysis is done after 24 hours of PGG (0.1 mg/mL) treatment as illustrated in FIG. 22.

Figure 23:
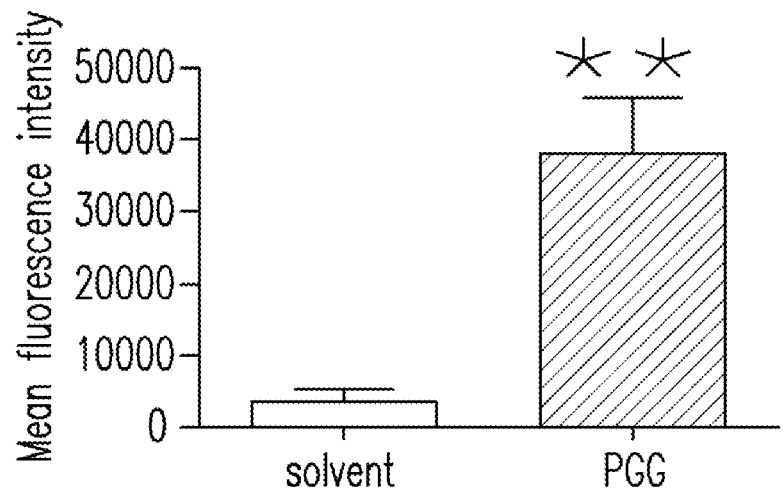
FIG. 23 illustrates fluorescence intensity in Annexin-V-positive cells among Huh7 cells.

Please refer to FIG. 23, which illustrates fluorescence intensity in Annexin-V-positive cells among Huh7 cells. Huh7 cells were harvested for Annexin V staining after PGG treatment.PGG can significantly induce apoptosis as illustrated in FIG. 23.

Figure 24:
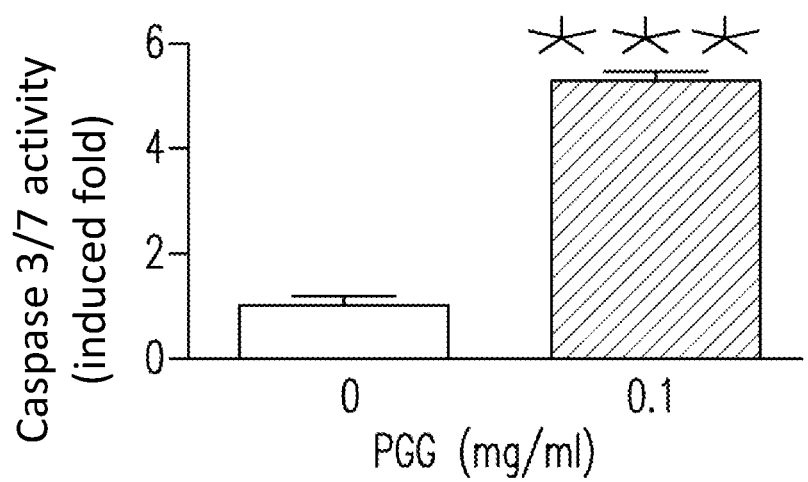
FIG. 24 illustrates PGG induced caspase 3/7 activity in Huh7 cells.

Please refer to FIG. 24, which illustrates PGG induced caspase 3/7 activity in Huh7 cells. Consistent with these findings, a five-fold increase in caspase 3/7 activity was observed in Huh7 cells after 12 hours of PGG treatment as illustrated in FIG. 24.

Immunoblot further confirmed that PGG treatment increased the level of cleaved caspase 3 in a dose-dependent manner. In summary, administration of PGG to Huh7 cells can induce apoptosis.

[PGG Sensitizes Huh7 Cells to Sorafenib Treatment]

To date, sorafenib is considered the drug of first choice for HCC, but its effectiveness is limited, and its side effects are still a major concern.

Figure 25:
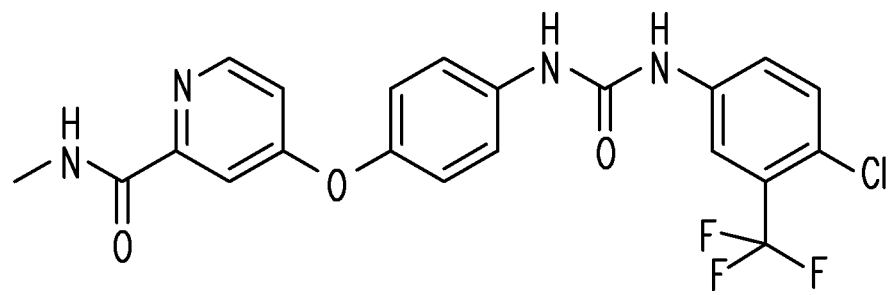
FIG. 25 illustrates the structural formula of sorafenib.

Please refer to FIG. 25, which illustrates the structural formula of sorafenib with a chemical name (4-[4-[[4-chloro-3-(trifluoromethyl)phenyl] carbamoylamino] phenoxy]-N-methyl-pyridine-2-carbox-amide)).

As described above, GNMT inhibits the bioactivity of hepatocellular tumor. To assess whether PGG can become a GNMT inducer, administering GNMT or PGG for treatments and see whether or not PGG sensitizes Huh7 cells to sorafenib treatment.

The cell viability is determined after Huh7-GFP cells capable of expressing Green fluorescent protein (GFP) and Huh7-GNMT cells are treated with an increased concentration of sorafenib.

Figure 26:
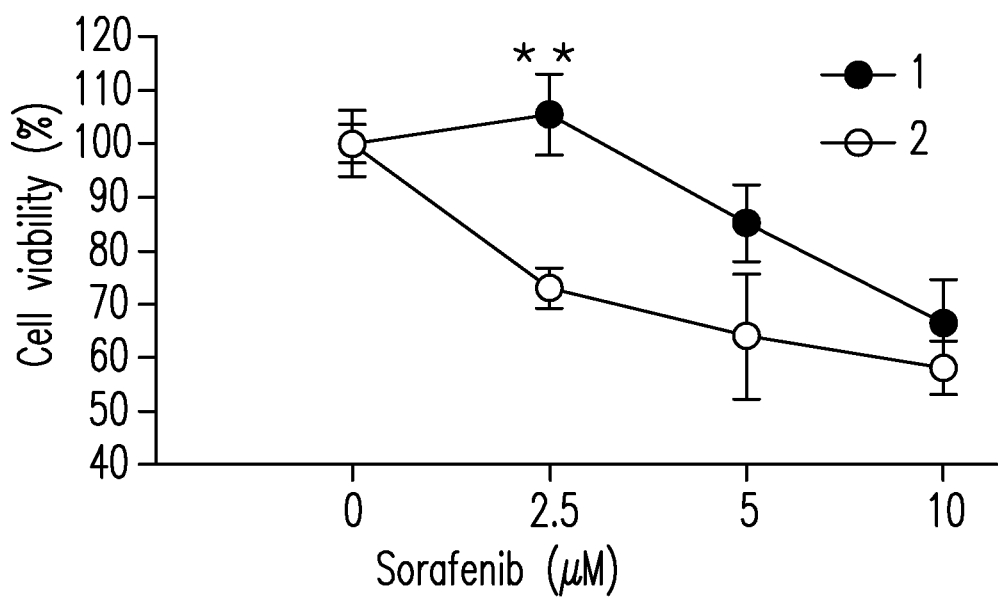
FIG. 26 illustrates the effect of sorafenib on cell proliferation, wherein numerals 1 and 2 denote Huh7-GFP cells and Huh7-GNMT respectively.

Please refer to FIG. 26, which illustrates the effect of sorafenib on cell proliferation, wherein numerals 1 and 2 denote Huh7-GFP cells and Huh7-GNMT respectively. Compared to the GFP control cells, the viability of GNMT stable cells decreased significantly in the presence of 2.5 μM sorafenib, which suggests that GNMT is able to sensitize HuH-7 cells to sorafenib treatment as illustrated in FIG. 26.

To assess the effect of additional GNMT to administering sorafenib, female nonobese diabetic/severe combined immunodeficiency (NOD-SCID) mice lacking thymus gland were subcutaneously injected with Huh7 cells or Huh7-GFP cells. The mice were randomly grouped and treated with a sorafenib or a physiological saline. Overexpression of GNMT inhibits cancer cell proliferation compared to the tumor due to Huh7-GFP cells. In oral administration of sorafenib (10 mpk), three days a week or physiological saline for treating mice, it was found that sorafenib significantly inhibits tumor growth.

Figure 27:
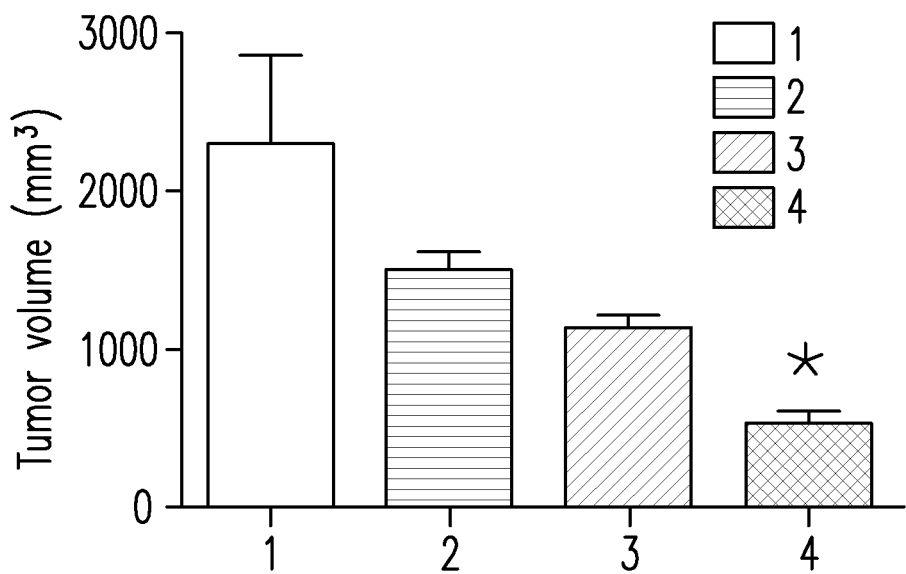
FIG. 27 illustrates that the tumor cells are treated with the compound of sorafenib, wherein the numeral 1 is for Huh7-GFP transfected cells administered with a physiological saline, the numeral 2 is for Huh7-GNMT transfected cells administered with a physiological saline, the numeral 3 is for Huh7-GFP transfected cells administered with 10 mg/kg (10 mpk) sorafenib, and the numeral 4 is for Huh7-GNMT transfected cells administered with 10 mg/kg (10 mpk) sorafenib.

Please refer to FIG. 27, which illustrates that the tumor cells are treated with the compound of sorafenib, wherein the numeral 1 is for Huh7-GFP transfected cells administered with a physiological saline, the numeral 2 is for Huh7-GNMT transfected cells administered with a physiological saline, the numeral 3 is for Huh7-GFP transfected cells administered with 10 mg/kg sorafenib and the numeral 4 is for Huh7-GNMT transfected cells administered with 10 mg/kg sorafenib. Compared with other groups, reducing the size of the tumor is statistically significant in Huh7-GNMT transfected cells administered with sorafenib. Based on the above results, a survey for the effect of PGG combined with sorafenib as a combination therapy to liver cancer was conducted.

[Combination Treatment of PGG and Sorafenib Exert Additive Toxicity Against HuH7 Cells]

Figure 28:
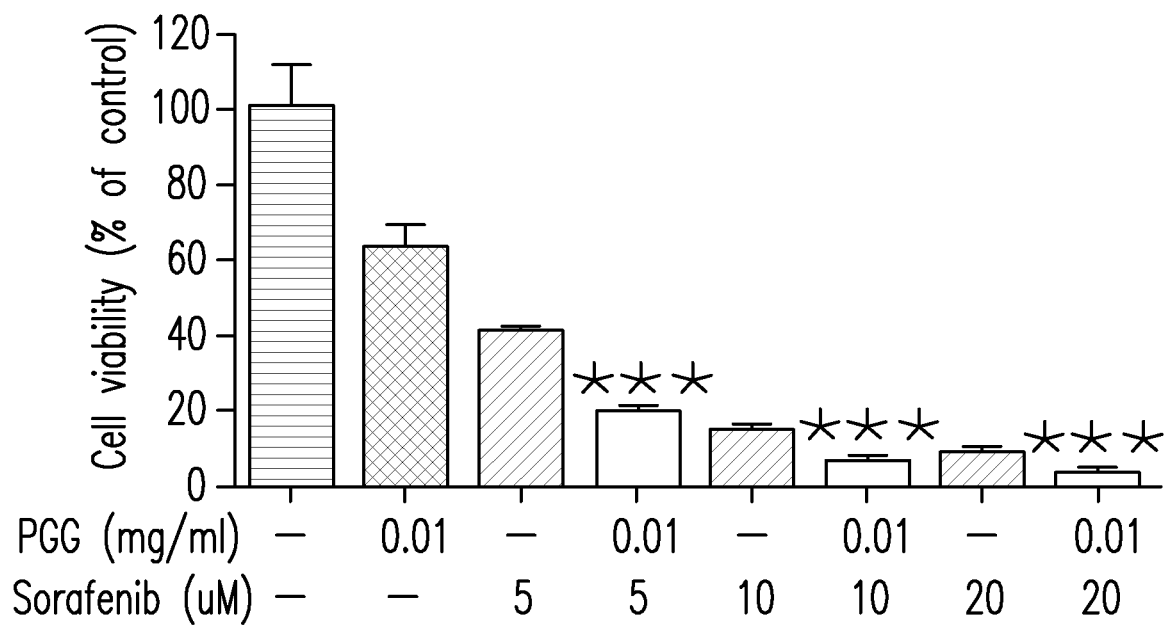
FIG. 28 illustrates the effects of PGG/sorafenib on cell viability.

Please refer to FIG. 28, which illustrates the effects of PGG/sorafenib on cell viability and it strengthens the effects of sorafenib after PGG is administered for 72 hours even though sorafenib is at a higher dose.

Figure 29:
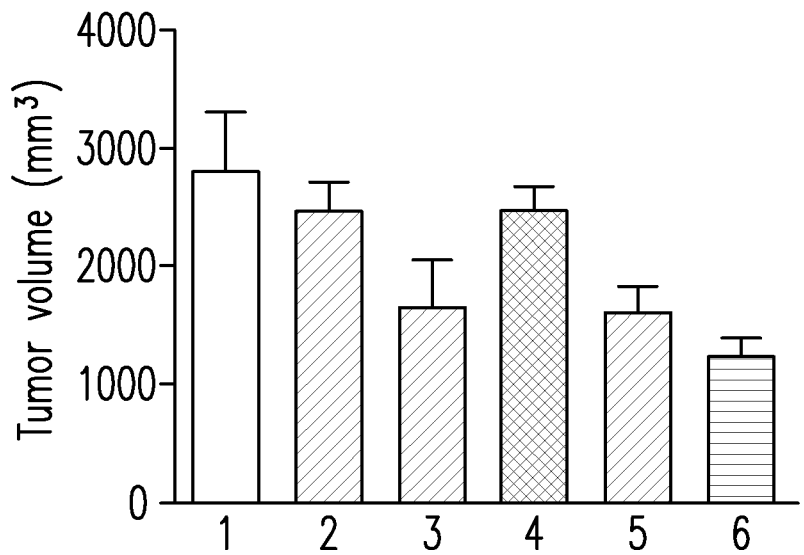
FIG. 29 illustrates the tumor volume, wherein the numeral 1 is for a physiological saline solution, the numeral 2 is for F3-6 (25 mg/kg (mpk)), the numeral 3 is for F3-6 (300 mpk), the numeral 4 is for sorafenib (10 mpk), the numeral 5 is for F3-6 (25 mpk) with sorafenib (10 mpk), and the numeral 6 is for PGG (25 mpk) with sorafenib (10 mpk)

Please refer to FIG. 29, which illustrates the tumor volume, wherein the numeral 1 is for a physiological saline solution, the numeral 2 is for F3-6 (25 mg/kg (mpk)), the numeral 3 is for F3-6 (300 mpk), the numeral 4 is for sorafenib (10 mpk), the numeral 5 is for F3-6 (25 mpk) with sorafenib (10 mpk), and the numeral 6 is for PGG (25 mpk) with sorafenib (10 mpk). In Huh7 cells xenograft in NOD-SCID mice, sorafenib (10 mpk) alone or combined with F3-6(25 mpk), F3-6(300 mpk) or not are all effective in inhibiting the tumor growth. F3-6 (25 mpk) with sorafenib (10 mpk) and PGG (25 mpk) with sorafenib (10 mpk) are most effective compared with any other treatments with a single drug.

Figure 30:
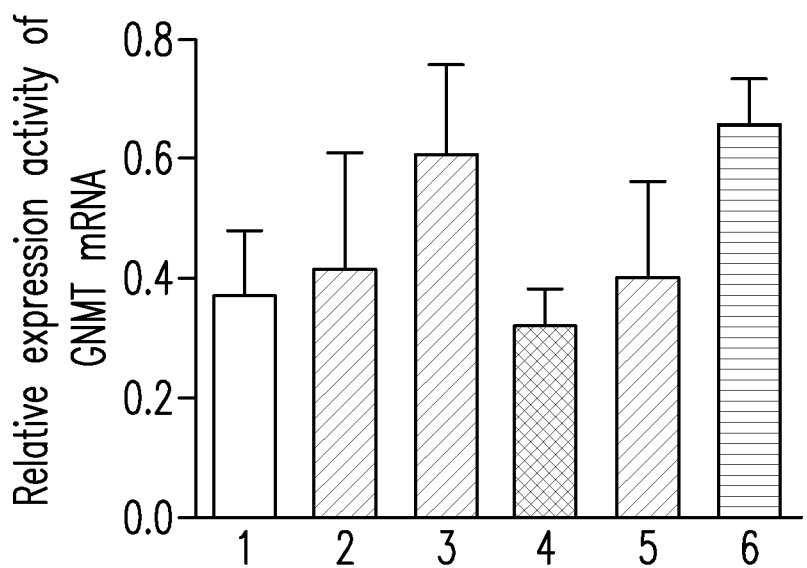
FIG. 30 illustrates the relative expression of GNMT mRNA in the tumor after treatments, wherein the numeral 1 is for a physiological saline solution, the numeral 2 is for F3-6 (25 mpk), the numeral 3 is for F3-6 (300 mpk), the numeral 4 is for sorafenib (10 mpk), the numeral 5 is for F3-6 (25 mpk) with sorafenib (10 mpk), and the numeral 6 is for PGG (25 mpk) with sorafenib (10 mpk)

Please refer to FIG. 30, which illustrates the relative expression of GNMT mRNA in the tumor xenograft mice after treatments, wherein the numeral 1 is for a physiological saline solution, the numeral 2 is for F3-6 (25 mpk), the numeral 3 is for F3-6 (300 mpk), the numeral 4 is for sorafenib (10 mpk), the numeral 5 is for F3-6 (25 mpk) with sorafenib (10 mpk), and the numeral 6 is for PGG (25 mpk) with sorafenib (10 mpk). The expression activity of GNMT mRNA is increased whenever fracrions F3-6 or PGG are administered.

[PGG Enhances GNMT Promoter Activity Via Suppression of c-Myc]

Table 2 shows signal transduction pathways and associated genes due to the impact of PGG.

TABLE 2

| Pathways | Associated genes due to PGG |
| --- | --- |
| Cancers | BIRC3, CCNE2, ETS1, JUP, EGLN1, FGF-2, TGFBR1, MYC |
| TGF-β | INHBE, ID4, TGFBR1, MYC |
| epidermal growth factor receptor | AREG, EREG, EIF4EBP1, MYC |
| cell cycle | ORC2L, CDKN2C, CCNE2, MYC |
| acute myeloid leukemia | EIF4EBP1, JUP, MYC |

[Use Microarray Analysis to Assess the Impact GNMT Expression Mechanism Due to PGG]

Pathway enrichment analysis is applied at 6 hours and 48 hours after Huh7 cells treated with PGG and it was found that 169 genes had changed significantly during the selected time periods.

This result shows that the following pathways are affected, including transforming growth factor-β (TGF-β) signal transduction pathway, cancer pathways, epidermal growth factor receptor (ErbB) signal transduction pathway, cell cycle pathways and acute myeloid leukemia pathways. As shown in Table 2, c-Myc gene is involved in all pathways.

Figure 31:
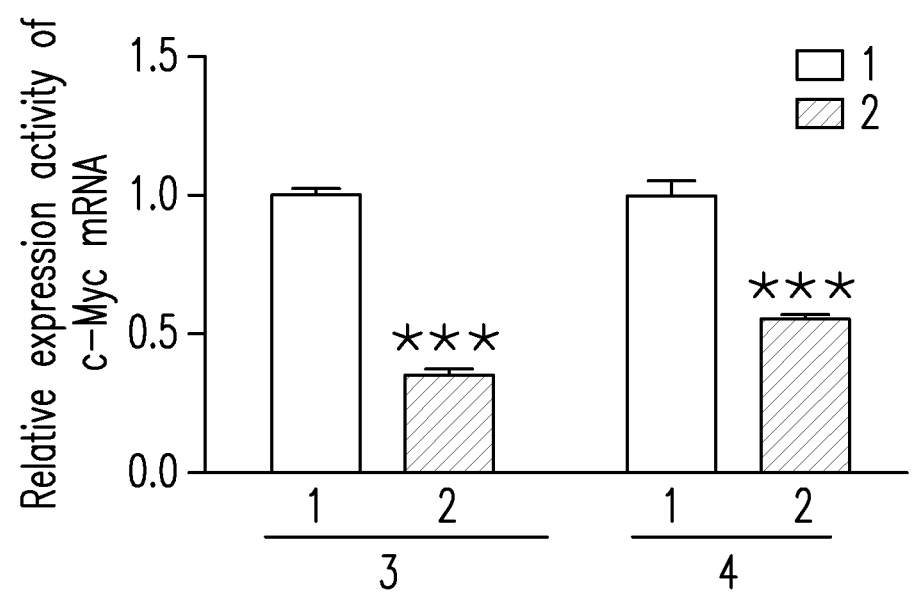
FIG. 31 illustrates the relative expression of c-Myc mRNA in the cells after treatments, wherein the numeral 1 denotes a solvent, the numeral 2 denotes PGG, the numeral 3 denotes Huh7 cells, and the numeral 4 denotes HepG2 cells.

Please refer to FIG. 31, which illustrates the relative expression of c-Myc mRNA in the cells after treatment by using Real-time Quantitative Polymerase Chain Reaction (qRT-PCR, Q-PCR), wherein the numeral 1 denotes a solvent, the numeral 2 denotes PGG, the numeral 3 denotes Huh7 cells, and the numeral 4 denotes HepG2 cells. In addition, the concentration of PGG was set as 0.1 mg/mL for FIGS. 31, 34, 39, 41, 42, 43, 46 and 47 respectively.

Figure 32A:
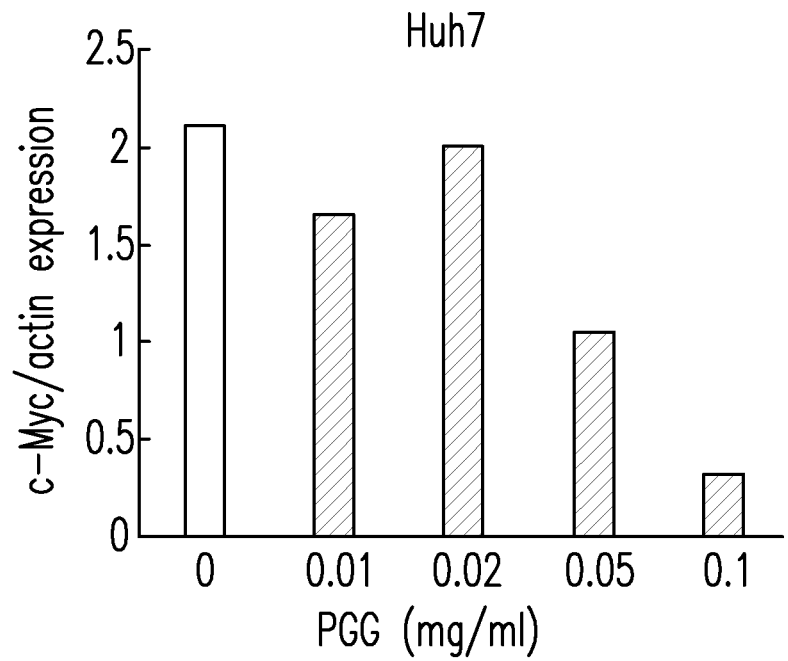
FIG. 32A illustrates PGG suppresses the expression of c-Myc protein in Huh7 cells in a dose-dependent manner.
Figure 32B:
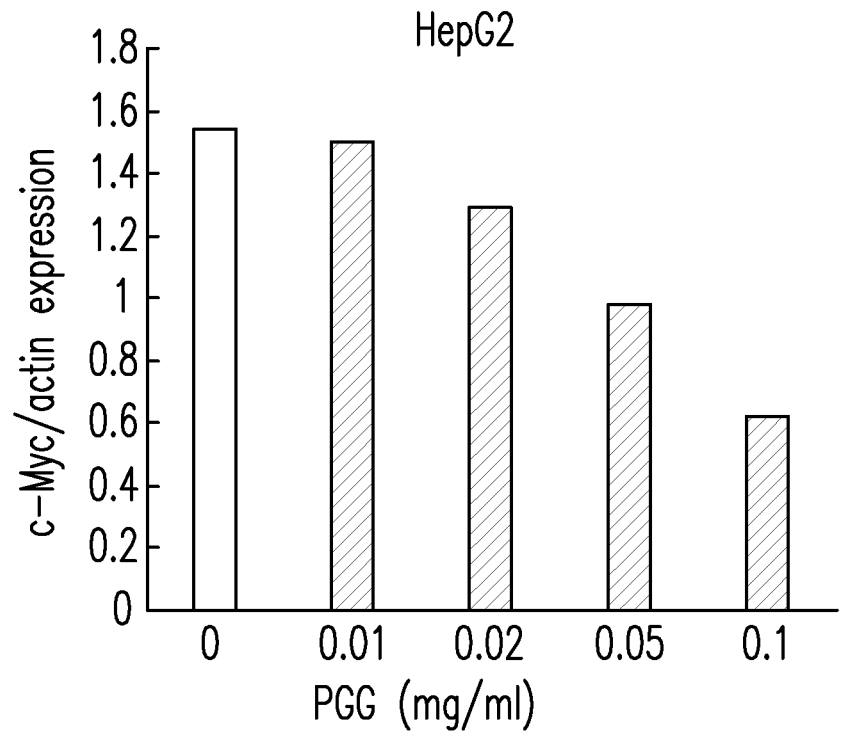
FIG. 32B illustrates PGG suppresses the expression of c-Myc protein in HepG2 cells in a dose-dependent manner.
Figure 33A:
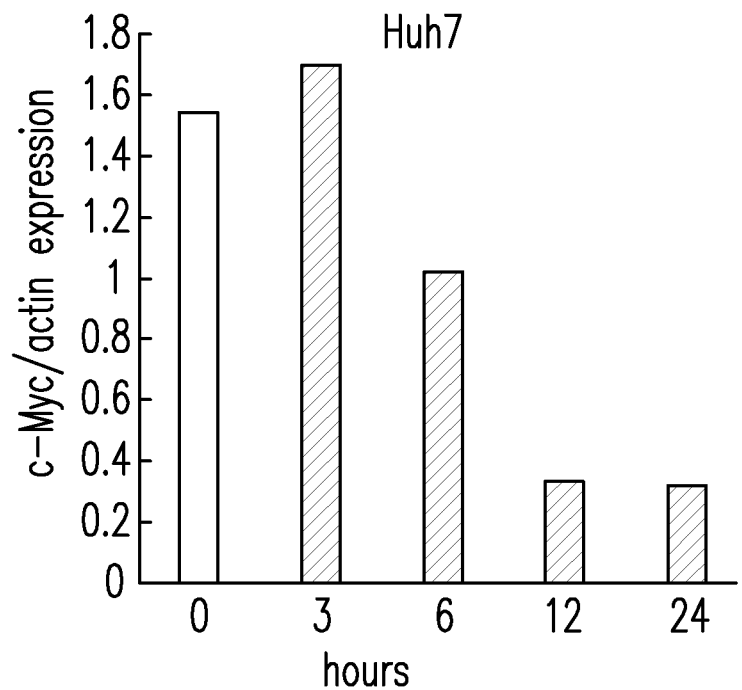
FIG. 33A illustrates PGG suppresses the expression of c-Myc protein in Huh7 cells in a time-dependent manner.
Figure 33B:
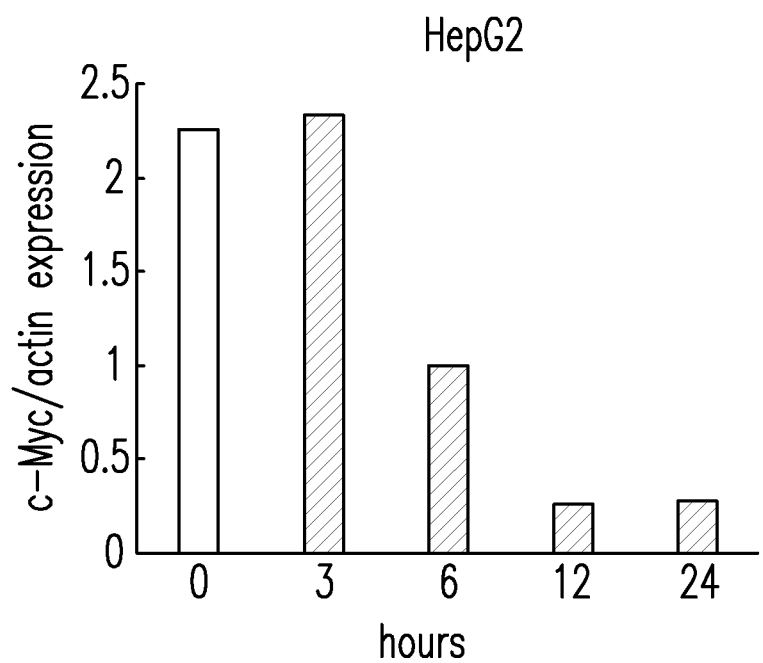
FIG. 33B illustrates PGG suppresses the expression of c-Myc protein in HepG2 cells in a time-dependent manner.
Figure 34:
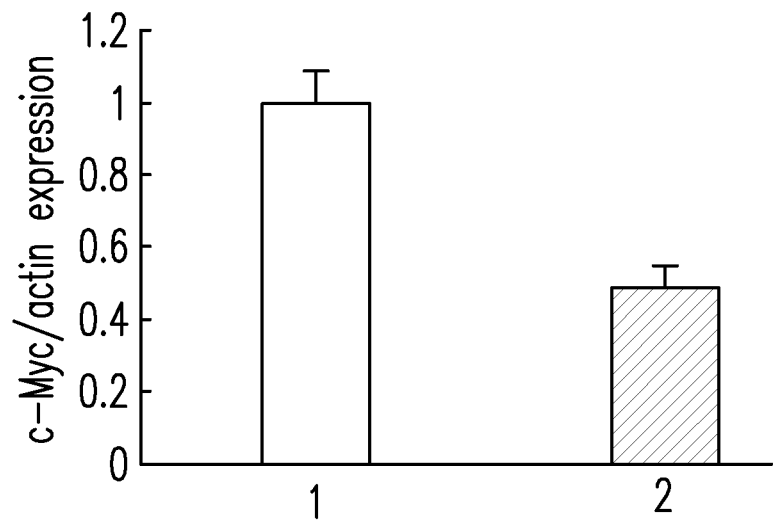
FIG. 34 illustrates c-Myc/actin expression ratio in the tumor after treatments, wherein the numeral 1 is for the solvent, and the numeral 2 is for PGG.
Figure 35:
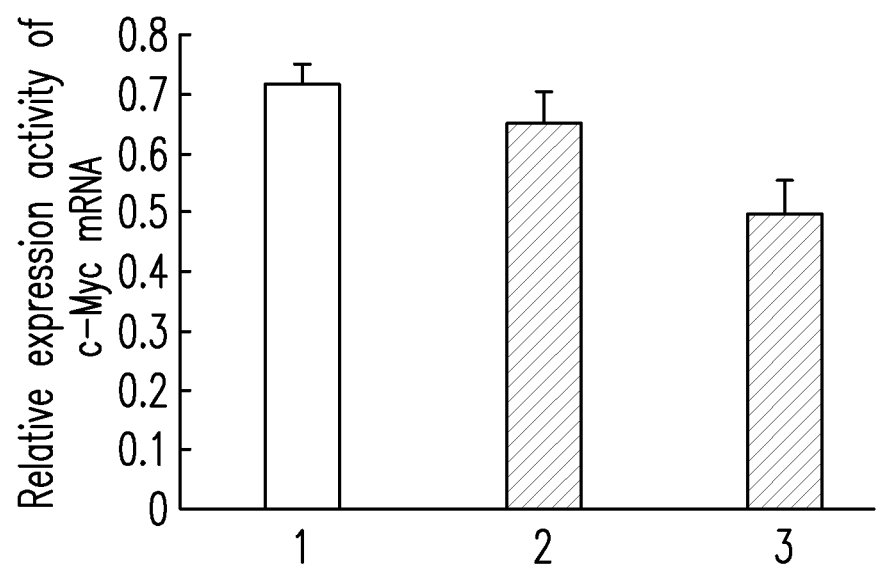
FIG. 35 illustrates c-Myc mRNA expression in the tumor after treatments, wherein the numeral 1 is for the solvent, the numeral 2 is for F3-6 (25 mpk), and the numeral 3 is for F3-6 (300 mpk)

Please refer to FIG. 32A, FIG. 32B, FIG. 33A and FIG. 33B. FIG. 32A illustrates PGG suppresses the expression of c-Myc protein in Huh7 cells in a dose-dependent manner. FIG. 32B illustrates PGG suppresses the expression of c-Myc protein in HepG2 cells in a dose-dependent manner. FIG. 33A illustrates PGG suppresses the expression of c-Myc protein in Huh7 cells in a time-dependent manner. FIG. 33B illustrates PGG suppresses the expression of c-Myc protein in HepG2 cells in a time-dependent manner. Thus PGG inhibits the expression of c-Myc gene a time-dependent manner and a dose-dependent manner by using immunoblotting Please refer to FIGS. 34-35. FIG. 34 illustrates c-Myc/actin expression ratio in the tumor after treatments, wherein the numeral 1 is for the solvent, and the numeral 2 is for PGG. FIG. 35 illustrates c-Myc in RNA expression in the tumor after treatments, wherein the numeral 1 is for the solvent, the numeral 2 is for F3-6 (25 mpk), and the numeral 3 is for F3-6 (300 mpk). Consistent with the results in vitro, it lowers the expression of c-Myc in the tumor xenograft mice treated with PGG or F3-6.

Since PGG downregulates c-Myc to affect GNMT promoter, it is deduced that knocking out c-Myc gene with short hairpin RNA (shRNA) could play a similar role as the therapeutic effect of PGG.

Huh7 cells were co-transfected with a GNMT promoter reporter plasmid, a thymidine kinase (TK) *renilla* luciferase plasmid, a shMyc plsmid or a shLacZ plasmid for 72 hours.

[A Test for GNMT Promoter Activity is Conducted Via Dual Luciferase Reporter Assays]

Figure 36:
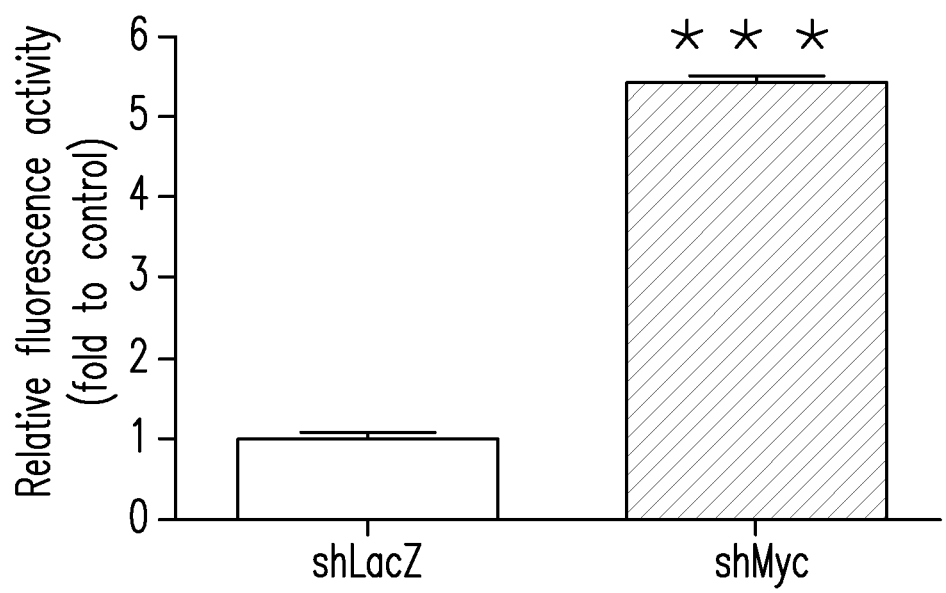
FIG. 36 illustrates relative fluorescence activity for the GNMT promoter.

Please refer to FIG. 36, which illustrates relative fluorescence activity for the GNMT promoter. It can be found that shRNA regulates c-Myc and makes it silent compared with the control group (shLacZ), resulting in a nearly 5 fold induction for GNMT promoter activity as shown in FIG. 36.

The c-Myc gene is knocked out through transformed Huh7-shMyc and Huh7-shLacZ stable cells in order to determine the expression of GNMT mRNA.

Figure 37:
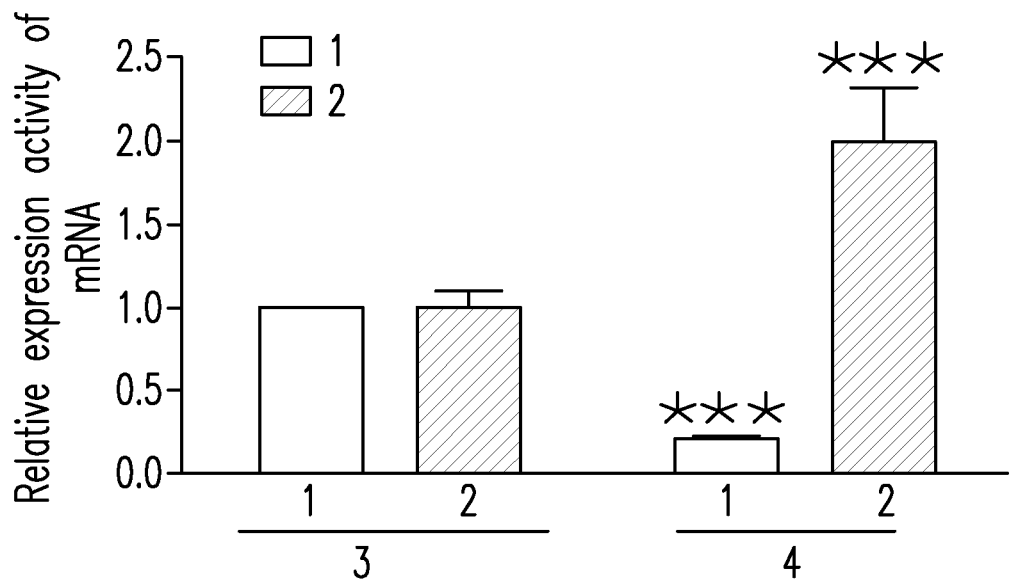
FIG. 37 illustrates relative expression activity of mRNA, wherein the numeral 1 denotes c-Myc, the numeral 2 denotes GNMT, the numeral 3 denotes shLacZ, and the numeral 4 denotes shMyc.

Please refer to FIG. 37, which illustrates relative expression activity of mRNA, wherein the numeral 1 denotes c-Myc, the numeral 2 denotes GNMT, the numeral 3 denotes shLacZ, and the numeral 4 denotes shMyc. Compared with the control group (Huh7-shLacZ cells), it was found that endogenous GNMT mRNA in cells is increased significantly as illustrated in FIG. 37.

A GNMT promoter reporter gene and a thymidine kinase (TK) *renilla* reporter gene are used to test for the activity of GNMT promoter, and assess whether c-Myc could ectopically overexpress c-Myc or not to verify the impact of c-Myc on the GNMT promoter.

Figure 38:
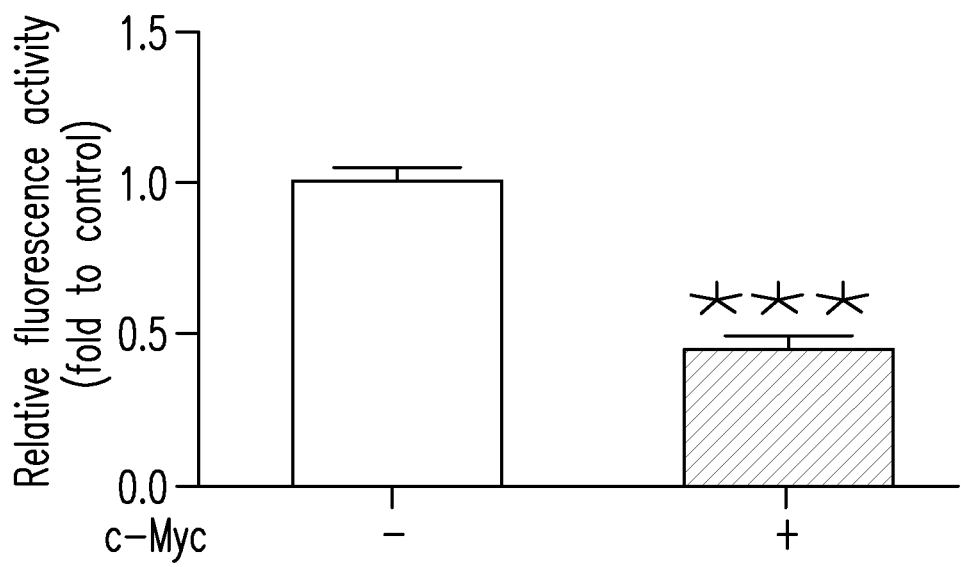
FIG. 38 illustrates GNMT promoter-driven luciferase inhibition is due to the overexpression of c-Myc.

Please refer to FIG. 38, which illustrates GNMT promoter-driven luciferase inhibition is due to the overexpression of c-Myc. The results show that overexpression of c-Myc results in the significant suppression of the activity of GNMT gene promoter-driven luciferase and the expression of endogenous GNMT protein as illustrated in FIG. 38. The results also show c-Myc downregulates the expression of GNMT, which is similar to the therapeutic effect of PGG.

Evaluating whether the activity of GNMT promoter is damaged or not by knocking out the c-Myc gene and then administering with PGG, in order to confirm that the inhibition of the expression of c-Myc resulting in induced GNMT promoter due to PGG.

Figure 39:
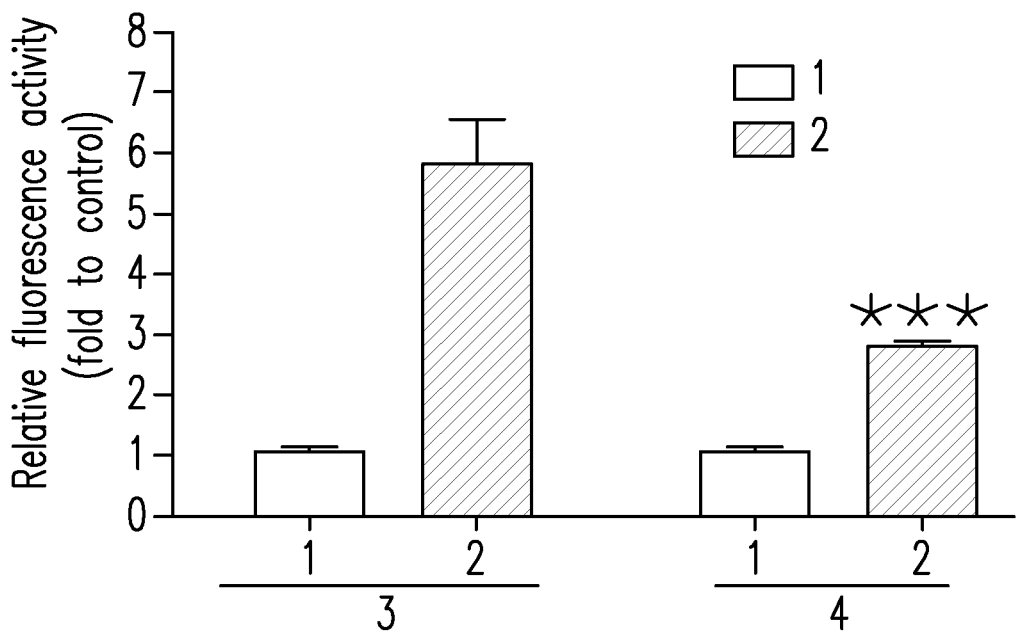
FIG. 39 illustrates overexpressions of PGG and c-Myc have influences on GNMT reporter, wherein the numeral 1 denotes the solvent, the numeral 2 denotes PGG, the numeral 3 denotes shLacZ, and the numeral 4 denotes shMyc.

Please refer to FIG. 39, which illustrates overexpressions of PGG and c-Myc have influences on GNMT reporter, wherein the numeral 1 denotes the solvent, the numeral 2 denotes PGG, the numeral 3 denotes shLacZ, and the numeral 4 denotes shMyc. As shown in FIG. 39, a drop due to the induced GNMT promoter by PGG can be seen in cells knocked out c-Myc. The above information indicates that downregulating c-Myc plays a dominant role in the induced GNMT promoter in Huh7 cells by PGG.

[The Anti-HCC Effect of PGG is Associated with c-Myc Suppression]

As to the mechanism for how to suppress the growth of liver cancer cells by PGG, it was deduced that by virtue of induced GNMT expression by PGG it could interfere liver cancer cells. And it can be expected to have the claimed therapeutic effect of PGG by knocking out GNMT. With transformed Huh7 cells, shRNAs which have stable expressions of GNMT are evaluated.

Figure 40:
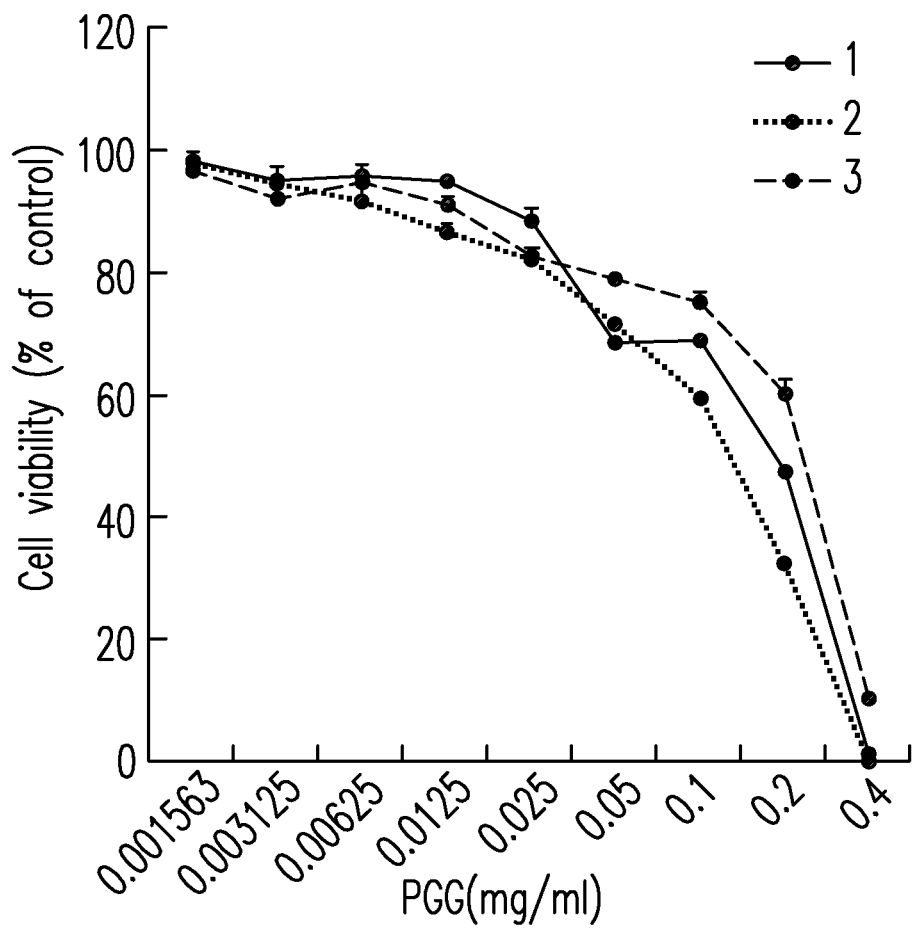
FIG. 40 illustrates PGG affects the viability in different cell lines, wherein the numeral 1 denotes shLacZ, the numeral 2 denotes shGNMT-1, and the numeral 3 denotes shGNMT-2.

Please refer to FIG. 40, which illustrates PGG affects the viability in different cell lines, wherein the numeral 1 denotes shLacZ, the numeral 2 denotes shGNMT-1, and the numeral 3 denotes shGNMT-2. Thus, there is no obvious improvement for the cytotoxicity caused by PGG, even though GNMT is knocked out.

Since the c-Myc is a well-known oncogene, it turns to test whether or not the downregulating function of c-Myc has influences on the effect of anti-hepatoma by PGG.

Figure 41:
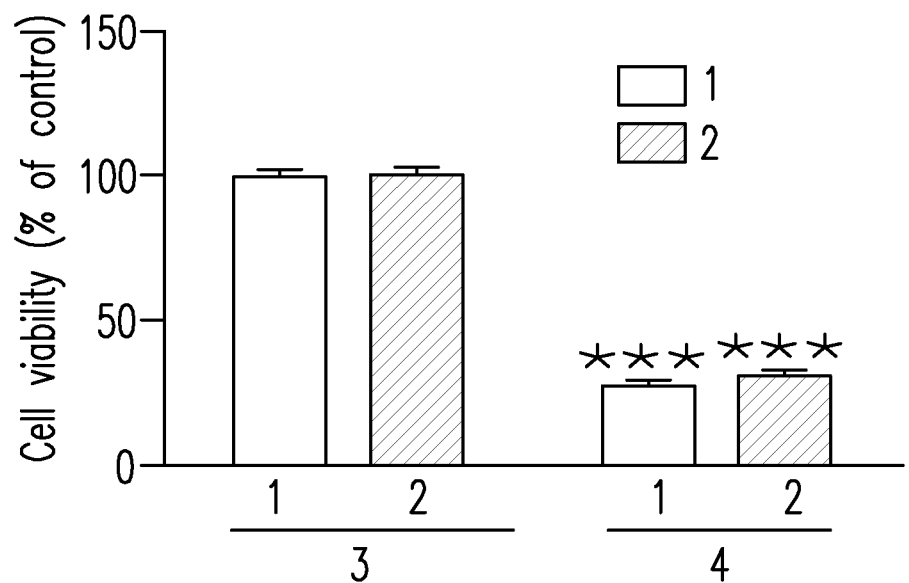
FIG. 41 illustrates the viability in Huh7 cells, wherein the numeral 1 denotes vehicle, the numeral 2 denotes c-Myc, the numeral 3 denotes solvent, and the numeral 4 denotes PGG.

Please refer to FIG. 41, which illustrates the viability in Huh7 cells, wherein the numeral 1 denotes vehicle, the numeral 2 denotes c-Myc, the numeral 3 denotes solvent, and the numeral 4 denotes PGG. For the question that whether or not ectopically overexpressed c-Myc can reduce PGG-induced cytotoxicity and affect liver cancer cells, it is found that Huh7 cells can not prevent the effects of PGG and there is still cytotoxicity as illustrated in FIG. 41.

Figure 42:
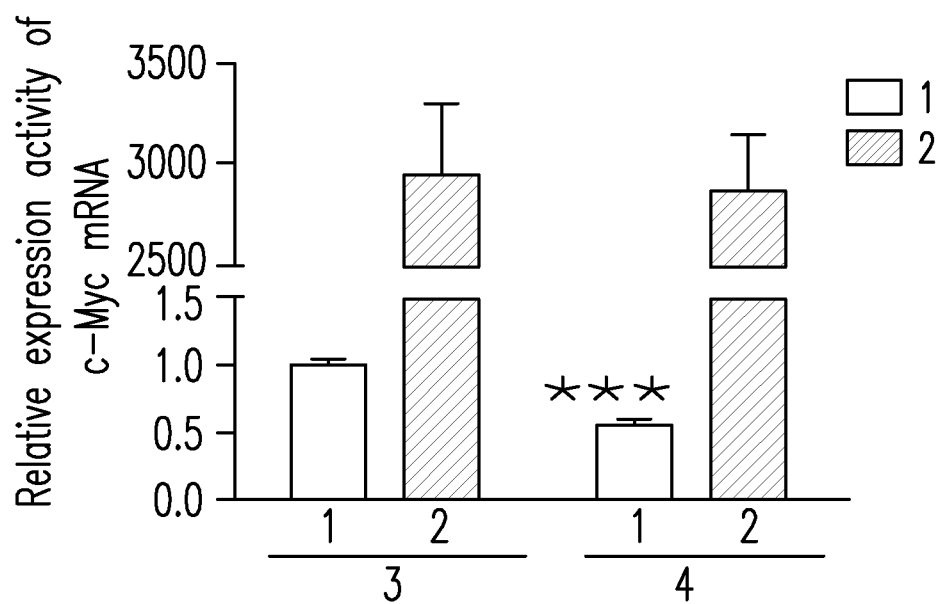
FIG. 42 illustrates PGG affects the expression activity of c-Myc mRNA in Huh7 cells, wherein the numeral 1 denotes vehicle, the numeral 2 denotes c-Myc, the numeral 3 denotes solvent, and the numeral 4 denotes PGG.

Please refer to FIG. 42, which illustrates PGG affects the expression activity of c-Myc mRNA in Huh7 cells, wherein the numeral 1 denotes vehicle, the numeral 2 denotes c-Myc, the numeral 3 denotes solvent, and the numeral 4 denotes PGG. Also ectopically overexpressed c-Myc can reduce the suppression of c-Myc mRNA induced by PGG, but it can not prevent the consumption of c-Myc protein in Huh7 cells induced by PGG as illustrated in FIG. 42. Therefore, PGG can reduce the stability of c-Myc protein.

Figure 43:
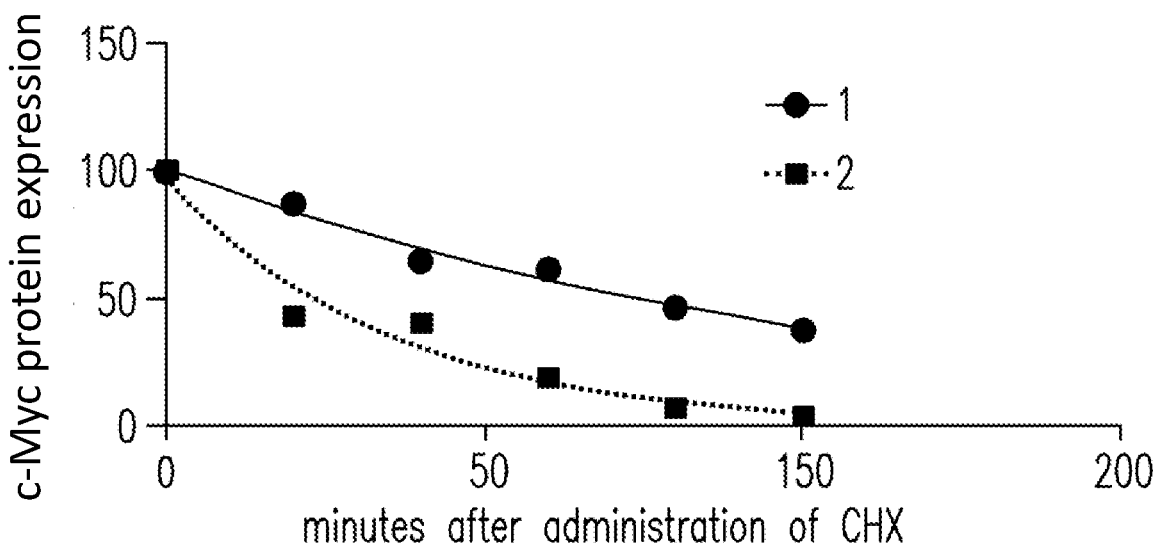
FIG. 43 illustrates c-Myc protein expression after cycloheximide (CHX) is given, wherein the numeral 1 denotes solvent, and the numeral 2 denotes PGG.

Please refer to FIG. 43, which illustrates c-Myc protein expression after cycloheximide (CHX) is given, wherein the numeral 1 denotes solvent, and the numeral 2 denotes PGG. Cycloheximide (CHX) is used for cycloheximide chase assay. After the PGG treatment, the degradation kinetics of c-Myc by using half-life measurement of proteins was determined. It is shown that PGG can significantly reduce the half-life of c-Myc protein as illustrated in FIG. 43. It is proven that PGG downregulates the expression of c-Myc protein via an enhanced protein degradation.

Based on the fact that PGG can interfere with the stability of c-Myc protein, using a knock out system is sufficient to play the role of c-Myc with respect to the induced cytotoxicity by PGG.

Figure 44:
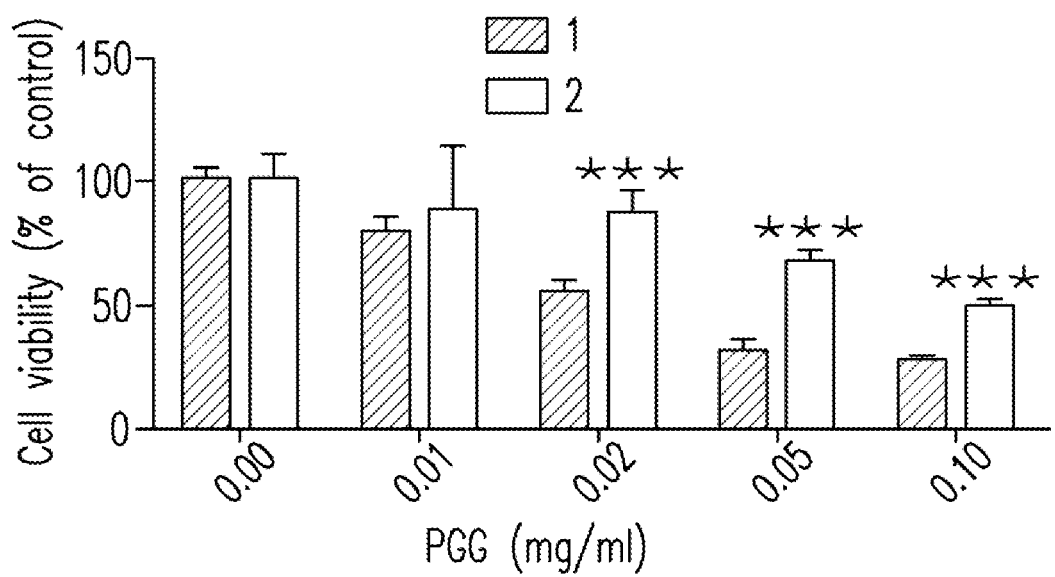
FIG. 44 illustrates the viability in Huh7 cells, wherein the numeral 1 denotes shLacZ, and the numeral 2 denotes shMyc.

Please refer to FIG. 44, which illustrates the viability in Huh7 cells, wherein the numeral 1 denotes shLacZ, and the numeral 2 denotes shMyc. Compared with Huh7-shLacZ cells, PGG can only slightly decrease cell viability of Huh7-shMyc cells as illustrated in FIG. 44.

The c-Myc gene knockout cells dominate the role of PGG killing cells. It is shown that the downregulating of c-Myc is the principal cause of PGG's influence on the growth of Huh7 cells.

To determine the proteolytic pathway and the induction of c-Myc protein degradation by PGG have relevance for each other and a variety of protein degradation inhibitors, an assessment of PGG regulating the degradation of c-Myc was conducted.

Figure 45:
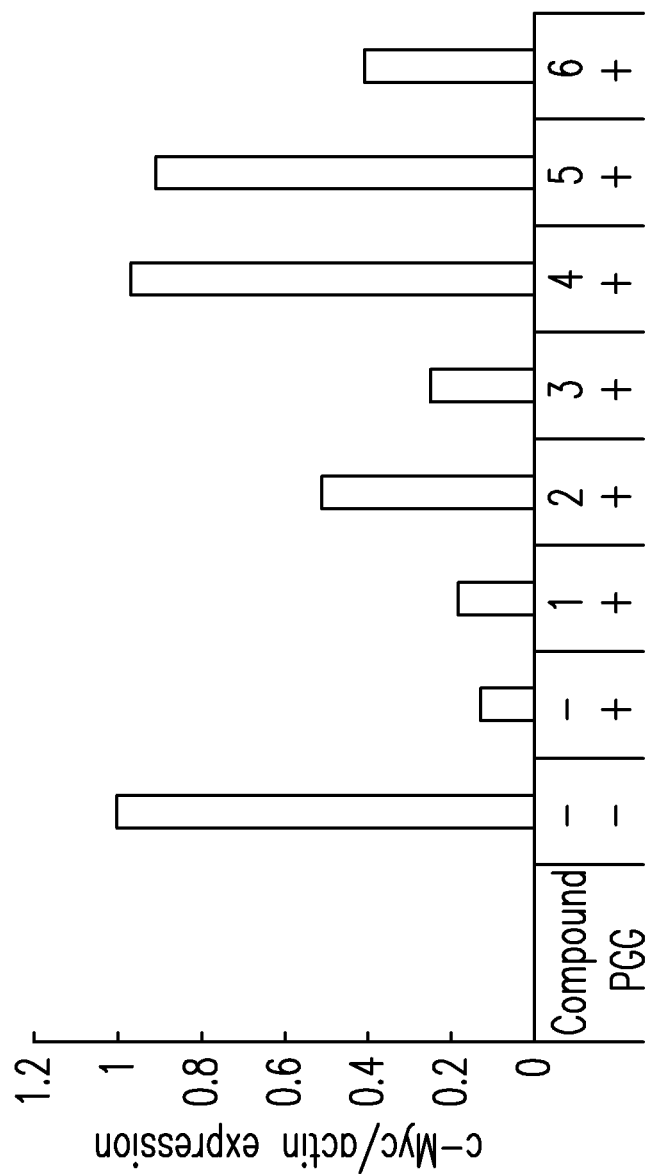
FIG. 45 illustrates c-Myc protein expression, wherein compounds 1-6 denote Z-LEU-LEU-LEU-CHO (MG132), ethylenediamine-tetraacetic acid (EDTA), $NH_4Cl$, chloroquine diphosphate, N-Benzyloxycarbonyl-Val-Ala-Asp (Ome)fluoromethyl ketone (Z-VAD-FMK) and N-Benzyloxy-carbonyl-L-leucyl-L-norleucinal (calpeptin) respectively.

Please refer to FIG. 45, which illustrates c-Myc protein expression, wherein compounds 1-6 denote Z-LEU-LEU-LEU-CHO (MG132), ethylenediamine-tetraacetic acid (EDTA), NH4Cl, chloroquine diphosphate, N-Benzyloxy-carbonyl-Val-Ala-Asp (Ome) fluoromethyl ketone (Z-VAD-FMK) and N-Benzyloxy-carbonyl-L-leucyl-L-norleucinal (calpeptin) respectively. It can be found that protease inhibitors such as NH$_4$Cl and Z-LEU-LEU-LEU-CHO (MG132) can not prevent the induction of c-Myc degradation caused by PGG; ethylenediamine-tetraacetic acid (EDTA), chloroquine diphosphate, N-Benzyloxy-carbonyl-L-leucyl-L-norleucinal (calpeptin), but an apoptosis inhibitor, N-Benzyloxycarbonyl-Val-Ala-Asp (Ome)fluoromethyl ketone (Z-VAD-FMK) can prevent an induced inhibition of c-Myc protein expression caused by PGG as illustrated in FIG. 45.

These results show that PGG in Huh7 cells induces a degradation of c-Myc protein via a proteasome independent mechanism.

We then determine whether or not it is a common phenomenon in tumor cells that the PGG induces an inhibition of c-Myc.

Figure 46:
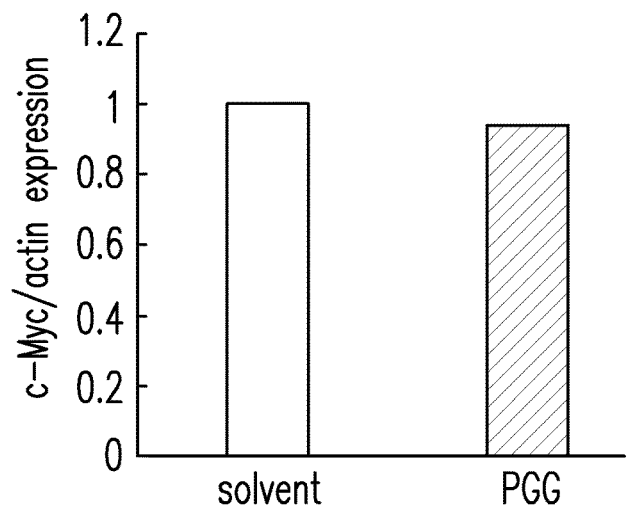
FIG. 46 illustrates PGG inhibits c-Myc protein expression in HL60 cells.

Please refer to FIG. 46, which illustrates the PGG inhibits c-Myc protein expression in HL60 cells.

Figure 47:
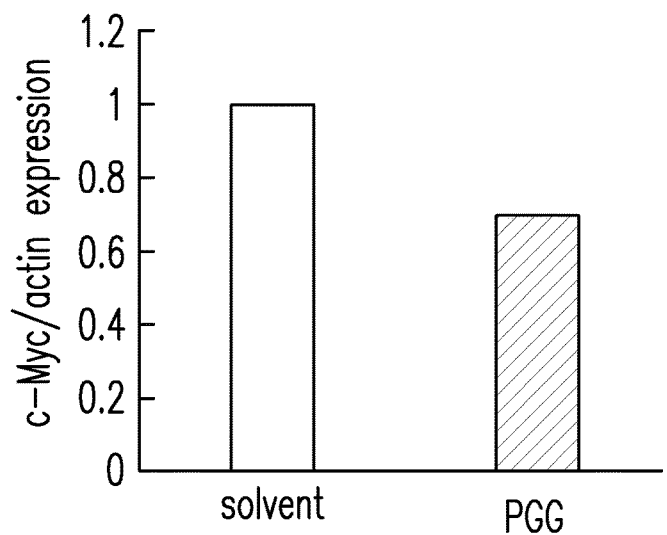
FIG. 47 illustrates PGG inhibits c-Myc protein expression in PC-3 cells.

Please refer to FIG. 47, which illustrates the PGG inhibits c-Myc protein expression in PC-3 cells. By using immunoblotting, it is also found that the PGG treatment can be used for other kinds of human tumors, such as prostate cancer cell line PC-3 (ATCC CRL-1435) and promyelocytic leukemia cell line HL-60 (ATCC CCL-240), in which c-Myc expression is reduced as illustrated in FIG. 46 and FIG. 47.

[Materials and Methods]

The present invention can be clarified based on the following exemplary embodiments; however, the present invention should not be limited by the following embodiments.

The drugs and biological materials used in the present invention are commercially available, and ways for preparation in the following are only for a few examples.

[Cell Culture and Reagents]

Human liver cancer cell lines Huh7, Hep G2, Hep 3B, SK-HEP-1, Mahlavu and embryonic kidney cell line HEK-293T all were cultured in Dulbecco's Modified Eagle's Medium (DMEM) (Gibco BRL, Grand Island, N.Y., USA) with 10% heat-inactivated fetal bovine serum (HyClone, Logan, Utah, USA), penicillin (100 U/mL), streptomycin (100 g/mL), nonessential amino acids (0.1 mM/L) and L-glutamine (2 mM/L) in a humidified incubator with 5% CO2.

Human prostate cancer cell line PC-3 and human promyelocytic leukemia cell line HL-60 were cultured in Gibco BRL company RPMI (Roswell Park Memorial Institute) 1640's medium.

Stablized cells comprises Huh7-GFP, Huh7-GNMT, Huh7-shGNMT, Huh7-shLacZ and Huh7-shMyc, which are established via the lentivirus system and cultured in Dulbecco's Modified Eagle's Medium (DMEM) (Gibco BRL, Grand Island, N.Y., USA) with 1 µg/ml puromycin.

Compounds 3-methyladenine (3-MA), Z-LEU-LEU-LEU-CHO (MG132), chloroquine diphosphate, (1 S,2 S)-2-(((S)-1-((4-Guanidinobutyl)amino)-4-methyl-1-oxopentan-2-yl)carbamoyl)cyclopropanecarboxylic acid (E-64), cycloheximide (CHX), N-isovaleryl-L-valyl-L-valyl-3-hydroxy-6-methyl-g-aminoheptanoyl-L-alanyl-3-hydroxyl-6-methyl-g-aminoheptanoic acid (pepstatin A) and propidium iodide were purchased from Sigma-Aldrich Corporation (St Louis, Mo., USA).

Compounds N-Benzyloxycarbonyl-Val-Ala-Asp(Ome) fluoromethyl ketone, Z-VAD-FMK were purchased from Selleckchem.com, while N-Benzyloxy-carbonyl-L-leucyl-L-norleucinal (calpeptin) were purchased from Millipore (Billerica, Mass., USA).

[Plasmids and Transfections]

Plasmids for lentivirus production (pCMV-ΔR8.91, pMD.G and pLKO.1), c-Myc, a short hairpin RNA (shRNA) of shRNA and β-galactosidase coded by LacZ gene were obtained from the National RNAi Core Facility (Academia Sinica, Taipei, Taiwan).

The GNMT promoter, the firefly luciferase reporter gene and Simian vacuolating virus 40 (SV40) late poly(A) signal elements were generated by digesting 1812/+14 GNMT promoter-luciferase plasmid with SspI and SalI. And pcDNA-c-Myc plasmid is provided by Dr. Liao of CMU.

For transfection, cells were plated to 70%-90% confluence, and plasmid DNAs were transfected by using Turbo-Fect Reagent (Fermentas, Hanover, Md., USA) and lipofectamine 3000 (Life Technologies, Mulgrave, Australia), with which it can be seen that the plasmid DNAs have been transfected.

[Establishment of GNMT Gene Expression-Oriented Platform for High-Throughput Screening]

The plasmid-pLKO.1 was purchased from RNAi Core (Academia Sinica). The U6 promoter fragment located within the ClaI and EcoRI site of pLKO.1 was replaced by a ClaI-BamHI-EcoRI (CBE) linker.

The CBE linker was generated by annealing two oligonucleotides: 5'-CGATATCGGATCCGTCGACG (SEQ ID NO. 1) and 5'-AATTCGTCGACGGATCCGATAT (SEQ ID NO. 2). The resultant double-stranded DNA fragment contained a 5' overhang end of ClaI followed by an EcoRV site, a BamH I site, a Sal I site and a 5' overhang end of EcoR I.

The CBE linker was ligated to ClaI and EcoRI digested pLKO.1 vector to generate pLV-CBE plasmid.

A ~4 kilobase (kb) fragment containing a synthetic poly (A) signal element (from the pGL3 promoter vector (Promega, Madison, Wis., USA)), the GNMT promoter, the firefly luciferase reporter gene and Simian vacuolating virus 40 (SV40) late poly(A) signal elements were generated by digesting 1812/+14 GNMT promoter-luciferase plasmid with SspI and SalI.

The resulting fragment was ligated into EcoRV and Sal I digested pLV-CBE plasmid. The resultant plasmid was designated as pLV-GNMTpLuc and was used for lentivirus production.

In brief, HEK293T cells were co-transfected with a packaging plasmid-pCMV-ΔR8.91, a VSV-G envelope-expressing plasmid-pMD.G and pLV-GNMTpLuc using Turbo-Fect™ Reagent (Fermentas).

Supernatant containing lentiviruses was harvested according to the protocol published on the website (http://rnai.genmed.sinica.edu.tw/).

Huh7 cells were infected with this virus and selected with puromycin-containing medium. One resultant colony was picked, amplified and denominated as H7GPL (Huh7 GNMT promoter-luciferase). The cell lysate of H7GPL was used for luciferase activity measurement using the Luciferase Assay System (Promega).

Assay quality is typically determined according to the Z' factor. To determine the quality of the platform for drug screening, the promoter activities were used to calculate the statistical parameters, such as the signal-to-background (S/B) ratio, the signal-to-noise (S/N) ratio and the value of the Z' factor.

[Drug Screening]

We used H7GPL cells and screened a library containing 324 pure compounds and 480 crude extracts prepared from traditional Chinese medicine and herbs which was provided by The National Research Institute of Chinese Medicine (NRICM).

H7GPL cells were seeded in 96-well plates and treated with control solvent (DMSO) at a concentration of 20 mg/mL and 480 crude extracts are in DMSO at a concentration of 200 mg/mL.

For primary screening, H7GPL cells seeded in 96-well plates were treated for 24 h with individual drugs at a concentration of 2 mg/mL for crude extracts and 0.2 mg/mL for pure compounds and then were lysed for the luciferase activity assay using the Luciferase Assay System (Promega, Madison, Wis., USA).

In each plate, six solvent control wells were treated with DMSO (the final concentration was 1%).

Reporter activity for each well was transformed to the Z score by using data from all assay plates.

Then, hits of primary screening were sorted by Z score ≥1.5 and used for secondary screening.

And then placed in the above-described culture plate H7GPL cell replication, and after the disposal of seized goods in those 20 hours, the company added AbD serotec Reagent (Oxford, UK), further cultured for 4 hours.

The cytotoxicity was measured according to the manufacturer's recommendation for assessing the reporter gene.

Drugs that induced GNMT promoter activity ≥1.5-fold were considered as hits of the secondary screen with the capability of enhancing the activity of GNMT.

[Quantitative Real-Time Polymerase. Chain Reaction 'qRT-PCR' Q-PCR]

RNA was prepared by using Tri Reagent (Sigma-Aldrich, St Louis, Mo., USA) and was reverse transcribed into cDNA using a Super Script II Reverse Transcriptase Kit (Invitrogen Inc., Carlsbad, Calif., USA).

PCR was performed on an ABI StepOne Plus System (Applied Biosystems, Foster City, Calif., USA) using the LightCycler® First Start DNA Master SYBR Green I reagent (Roche Diagnostics, Basel, Switzerland). The mRNA level was normalized using the TATA-box binding protein (TBP) mRNA level as the standard.

The following primers were used: GNMT forward, 5'-ACTGGATGACT CTGGACAA-3' (SEQ ID NO. 3) and reverse, 5'-ACTGAGGATGTGGTCGT-3'(SEQ ID NO. 4); TBP forward, 5'-TGCACAGGAGCCAAGAGTGAA-3' (SEQ ID NO. 5) and reverse, 5'-CACATCACAGCTCCC-CACCA-3'(SEQ ID NO. 6); c-Myc forward, TTCGGTTGTTGCTGATCTGTCT(SEQ ID NO. 7) and and reverse, CCCTCCACTCGGAAGGACTAT(SEQ ID NO. 8).

[Immunoblotting]

Cells or xenograft tumors were harvested with RIPA lysis buffer (50 mM Tris (pH 7.5), 150 mM NaCl, 1% Triton X-100, 0.1% sodium dodecyl sulfate (SDS), 0.5% sodium deoxycholate, supplemented with protease and phosphatase inhibitors (1 mM Phenylmethanesulfonyl Fluoride (PMSF), 10 g/mL leupeptin, 50 g/mL Tosyllysine Chloromethyl Ketone (TLCK), 50 g/mL Tosyl phenylalanyl chloromethyl ketone (TPCK), 1 g/mL aprotinin, 1 mM sodium fluoride (NaF), 5 mM sodium pyrophosphate (NaPPi) and 10 mM sodium orthovanadate ($Na_3VO_4$)).

Protein lysates were quantified and separated on SDS-PAGE gel, and immunoblotting was carried out.

The following antibodies were used: anti-GNMT (14-1, YMAC Bio Tech, Taiwan), anti-caspase-3 (9H19L2, Thermo Scientific) and anti-actin (AC-15, Sigma-Aldrich).

[Cell Viability and Colony Formation Assay]

AlamarBlue® assay (AbD Serotec, Raleigh, N.C., USA) was used to evaluate the cytotoxic effects of the tested drugs according to the manufacturer's recommendation. For the colony assay, Huh7 cells were seeded ($1 \times 10^4$ cells/well) in 6-well plates. After an overnight incubation, cells were treated with drugs at the specified concentrations for 7 days. Numbers of surviving colonies were analyzed through the crystal violet staining method. Colonies were quantified by OpenCFU colony counting software (http://opencfu.sourceforge).

[Extraction, Isolation and Identification of GNMT Enhancer Compounds]

Example 1: Preparation for the Bioactive Fractions of *Paeonia lactiflora* Pall

As shown in scheme 1, about 150 g of the ground material was reflux extracted twice with 0.6 L of 50% aqueous MeOH for 1 h each. The supernatant was filtered through a filter paper, combined and partitioned three times with 0.7 L ethyl acetate each. The initial fractionation of the ethyl acetate extract was conducted by using an MPLC system (300×30 mm, silica gel, 40-63 μm; Merck, Germany). Dichloromethane (A) and MeOH (B) were used as the mobile phase (gradient conditions: 100% A for 1 h, to 40% B in 20 min and then to 100% B in 20 min, flow rate: 18 mL/min). The collected fractions were assayed by TLC (silica gel 60 F254 plates; Merck, Germany), using a mixture of ethyl acetate, MeOH and 0.1% acetic acid (15:2:0.5) as the mobile phase. Results were evaluated at 254 nm and by spraying with vanillin/sulfuric acid reagent. The luciferase assay was used to identify eight active fractions in PL extract as described above. Further purification of the most active fraction (F3) was performed on a Sephadex LH-20 column using MeOH as the mobile phase and obtained the bioactive fractions of F3-6.

Example 2: Preparation for a Compound of 1,2,3,4,6-penta-O-galloyl-β-D-glucopyranoside (PGG)

The fraction F3-6 was further purified by a HPLC system, Agilent 1100 series coupled with a photodiode array detector. An RP-18 column (Cosmosil, 250×10 mm, 5 μm; nacalai, Japan) was used. Water (A) and CH3CN (B), with 0.1% acetic acid each, were used as the mobile phase (gradient conditions: 5% B for 20 min, to 100% B, flow rate: 3 mL/min). Monitoring the separation at 203 nm led to the isolation of the effective compound, 1,2,3,4,6-penta-O-galloyl-β-D-glucopyranoside (PGG). PGG was obtained as a pale brown, amorphous powder with UV maxima at 211, 231 and 278 nm as illustrated in FIG. 15. For MS analysis, PGG was diluted in MeOH and directly infused into a Finnigan MATLCQ. The mass spectra were recorded in the positive and negative ESI mode and showed an m/z value of 963.02 $[M+Na]^+$ and 939.03 $[M-H]^-$, respectively. NMR spectra of the isolated compound in deuterated methanol (CD3OD) were recorded on a VNMRS 600 NMR spectrometer (Varian, Palo Alto, Calif., USA). Identification was achieved by the comparison of the spectroscopic data obtained with those in the literature. PGG was dissolved in Phosphate buffered saline (PBS) for the cell-based assay.

Example 3: Preparation for Fractions of Galla Chinesis

As shown in the planning scheme 1, Galla Chinesis was obtained from a local Chinese drug store. About 105 g of the ground material was reflux extracted twice with 0.6 L of 50% MeOH(aq) for 1 h each. The supernatant was filtered through a filter paper, combined, and dried under reduced pressure. The crude extract (90.6 g) was conducted by using an absorption/detaching process. The 450 g silica gel (40-63 µm; Merck, Germany) was mixed with partial dried crude extract, and dried by reduced pressure. Dichloromethane, methanol, ethyl acetate, and 0.1% acetic acid were used as washing solutions. The E1 fraction (GC_E1) was washed-out by dichloromethane:methanol=90:10. The E2 fraction (GC_E2) was detached by using ethyl acetate:methanol: 0.1% acetic acid=15:2:0.5, and then the E3 fraction (GC_E3) was washed by 100% methanol. The collected fractions were assayed by TLC (silica gel 60 F254 plates; Merck, Germany), using a mixture of ethyl acetate, methanol, and 0.1% acetic acid (15:2:0.5) as mobile phase. Results were evaluated at 254 nm and 360 nm and by spraying with vanillin/sulfuric acid reagent. Further purification of the most active fraction (GC_E2) was performed on a Sephadex LH-20 column using methanol as mobile phase and led to the isolation of GC_E2_CF6. The GC_E2_CF6 was obtained as a pale brown, amorphous powder.

Example 4: Fingerprints of GC_E2_CF6 from Galla Chinesis

The Waters Acquity UPLC system, coupled with Waters photodiode array detector, was used for UPLC analysis. Analysis was carried out at 35 □ on a Thermo Syncronis C18 (100×2.1 mm, 1.7 µm) column. A linear gradient elution of eluents A (Acetonitrile) and B (0.1% phosphate) was used for the separation. The elution program was conducted as follows: 2% of A was held for first 1 min, a linear gradient of 2-10% A within the first 1-2 min, 10% A held for 2 minutes, a linear gradient of 10-25% A within the range of 4-10 min, and then, a linear gradient of 25-50% A within the range of 10-14 min. This was followed by a 1 min 100% A clean up and 5 min equilibration period prior to the injection of each sample. The peaks were monitored at 203 nm. The solvent flow rate was kept at 0.4 mL min$^{-1}$ and the injection volume was 1 µL.

[Flow Cytometry Assay]

Cells were harvested and fixed with cold 75% ethanol overnight and stained with propidium iodide (10 ug/mL) and RNase A (1 mg/mL) at 37 □ for 30 min. The cells were then analyzed by an Accuri C6 Flow cytometer (BD Biosciences, San Jose, Calif., USA). Cells were stained for Annexin V—APC Apoptosis Detection Kit according to the manufacturer's protocol (eBioscience, San Diego, Calif., USA).

[Caspase 3/7 Activity Assay]

Huh7 cells were plated in 96-well plate and treated with solvent or PGG for 12 h. To measure caspase-3 and caspase-7 activation, the Apo-ONE® Homogeneous Caspase-3/7 assay was performed according to the Promega Technical Bulletin-Apo-ONE® Homogeneous Caspase-3/7 assay.

[Microarray Analysis]

According to the manual of Affymetrix GeneChip expression analysis operation, array hybridization is done. And raw data is normalized using the Affymetrix (USA) Exprssion Console™ software. Using t-test statistic to determine the treatment group and the control group, the significant changed probe sets have a q value <0.005 and a q value of the mean-diff is greater 1.5. Differentially expressed genes probe set is processed with DAVID (Database for Annotation, Visualization and Integrated Discovery; http://david.abcc.ncifcrf.gov/) Bioinformatics online tools for annotation and pathway enrichment analysis.

[In Vivo Tumor Models]

All animal experiments were reviewed and approved by the Institutional Animal Care and Use Committee of Kaohsiung Medical University (city, country) and performed in accordance with relevant guidelines. For the tumor incidence assay, 5-6-week-old female non-obese diabetic-severe combined immunodeficiency (NOD-SCID) mice were subcutaneously injected with Huh7 cells (1×10$^6$) in the right flank. Five days after transplantation, mice were randomly divided into 3 groups and were treated with F3-6 (25 mg/kg (mpk) by i.p injection and 300 mpk by oral administration) and vehicle three times per week as illustrated in FIGS. 13 and 14.

In addition, to assess the combinatory effect of GNMT and sorafenib, female nonobese diabetic/severe combined immunodeficiency (NOD-SCID) mice lacking thymus gland were subcutaneously injected with Huh7 cells or Huh7-GFP cells (2×10$^6$).

When the tumors of the mice were detected in a significantly growing status, showing the same xenograft, the mice were randomly divided into two groups and treated with 10 mg/kg LC Laboratories sorafenib or physiological saline three times per week as illustrated in FIG. 27.

By the same token, mice were subcutaneously injected with Huh7 cells (2×10$^6$) in order to test the anti-tumor effect of PGG in vivo.

When the tumors of mice are detected in a significantly growing status, the mice are randomly divided into two groups and treated with PGG and physiological saline once a day for 10 days and the tumor volume after the treatment is measured as illustrated in FIG. 20.

To assess the combinatory effect of drugs, female nonobese diabetic/severe combined immunodeficiency (NOD-SCID) mice lacking thymus gland were injected with Huh7 cells (2×10$^6$).

When the tumors of the mice are detected in a significantly growing status, the mice are randomly divided into six groups with respective treatments: a physiological saline solution, F3-6 (25 mg/kg (mpk)), F3-6 (300 mpk), sorafenib (10 mpk), F3-6 (25 mpk) with sorafenib (10 mpk), and PGG (25 mpk) with sorafenib (10 mpk).

Mice are administered F3-6 (25 mpk), F3-6 (300 mpk) or PGG (25 mpk) three times per week, and sorafenib (10 mpk) twice per week alone or combined with F3-6 or PGG as illustrated in FIG. 29.

Tumor growth was monitored (every day or three times per week) by using Vernier caliper measurement of the length (L) and width (W) of the tumor.

Tumor volume (TV) was calculated by using the formula volume=(L×W$^2$)/2.

F3-6 was dissolved in PBS, PGG was dissolved in PBS or 0.5% carboxymethyl cellulose sodium salt, while sorafenib was dissolved in polyoxyethylene castor oil (Cremophor EL)/ethanol solution.

[Statistical Analysis]

The results are represented as Mean±SEM. Statistical differences between the unpaired and paired samples are analyzed by non-dependent Student's t-test. Whenever multiple treatment groups are compared with the control group, one way ANOVA or two way repeated measures ANOVA are applied. Whenever the analysis of variance (ANOVA) showed a significant difference, Dunnett's test or Student-Newman-Keuls test was applied and $p<0.05$ was considered statistically significant. As for data and graphic analysis, SigmaPlot software (version 8.0, Chicago, Ill., USA) and SigmaStat (version 2.03, Chicago, Ill., USA) are applied, running on an IBM computer.

CONCLUSION OF THE PRESENT INVENTION

In summary, one purpose of the present application is to establish a drug screen platform for identification of novel drugs for prevention and treatment of liver diseases and then verify the platform. Another purpose of the present application is to find two kinds of candidate drugs, one of which has been verified in a mouse model. The two drugs both have a protective effect for liver, and can be used in prevention and treatment for liver diseases, such as fatty liver, liver fibrosis, liver sclerosis and liver cancer. To overcome the disadvantages of the prior art, the present invention explores the bioactivity of 1,2,3,4,6-penta-O-galloyl-Beta-D-glucopyranoside (PGG), or the use of composition or foods in combination with sorafenib through experiments. According to the present invention, PGG can be extracted from *Paeonia lactiflora* Pall. or Galla Chinesis in some embodiments.

The present invention is related to building up a GNMT promoter-driven luciferase reporter assay in order to identify bioactive compounds associated with GNMT. It can be found that 1,2,3,4,6-penta-O-galloyl-Beta-D-gluco-pyranoside (PGG) in natural form is a candidate compound. In addition, PGG is experimentally confirmed that it facilitates the cytotoxicity of sorafenib to Huh7 cells in a combination therapy in vitro, while PGG inhibits tumor cells growth in vivo. In addition, PGG not only inhibits the expression of c-Myc gene, but also induces a degradation of c-Myc protein. Obviously, PGG is a novel type of c-Myc inhibitor and a candidate drug to hepatocellular carcinoma.

EMBODIMENTS

1. A composition for inhibiting a liver tumor in an organism, comprising: an activator being 1,2,3,4,6-penta-O-galloyl-Beta-D-glucopyranoside (PGG), wherein PGG is extracted from at least one of *Paeonia lactiflora* Pall. and Galla Chinesis.
2. The composition of Embodiment 1, wherein PGG has an electrospray ionization mass being m/z 963.02 [M+Na]+ and 939.03 [M-H]-.
3. The composition of any one of Embodiments 1-2, wherein PGG extracted from *Paeonia lactiflora* Pall. is further extracted via first a methanol, and separated by a medium-pressure liquid chromatography (MPLC) and a Sephadex LH-20 column respectively with the following conditions: in the MPLC, using a dichloromethane and a second methanol as solvents in a mobile phase with concentration gradient conditions: 100% dichloromethane to 60% dichloromethane/40% methanol for 1 hour, 60% dichloromethane and 40% methanol to 100% methanol for 20 minutes and then 100% methanol for 20 minutes, and in the Sephadex LH-20 column, using a third methanol as a solvent in a mobile phase with flow rate: 18 mL/minute.
4. The composition of any one of Embodiments 1-3, wherein the PGG extracted from Galla Chinesis is further extracted via a first methanol, and separated by a medium-pressure liquid chromatography (MPLC) and a Sephadex LH-20 column respectively with the following conditions: in the MPLC, an E1 fraction washed-out by dichloromethane:methanol=90:10, an E2 fraction washed-out by ethyl acetate:methanol:0.1% acetic acid=15:2:0.5, an E3 fraction washed-out by 100% methanol, and in the Sephadex LH-20 column, using a second methanol as a mobile phase.
5. The composition of any one of Embodiments 1-4, further comprising a compound of sorafenib.
6. The composition of any one of Embodiments 1-5, wherein the composition is one of a food and a medicine.
7. The composition of any one of Embodiments 1-6, wherein the composition is used to enhance an expression of a Glycine N-methyltransferase (GNMT) and inhibit an expression of a c-Myc protein.
8. The composition of any one of Embodiments 1-7, further comprising one of a pharmaceutically acceptable excipient and a pharmaceutically acceptable carrier.
9. A method of manufacturing a pharmaceutical composition for a treatment of a liver cancer, the pharmaceutical composition comprising a compound of 1,2,3,4,6-penta-O-galloyl-Beta-D-glucopyranoside (PGG).
10. The method of Embodiment 9, wherein the pharmaceutical composition is used for at least one of the group consisting of curing a liver disease, a prostate cancer and a human promyelocytic leukemia.
11. The method of any one of Embodiments 9-10, wherein the pharmaceutical composition combined with a sorafenib is administered to a subject by a multi-administered method.
12. The method of any one of Embodiments 9-11, wherein the PGG is extracted from at least one of *Paeonia lactiflora* Pall. and Galla Chinesis.
13. The method of any one of Embodiments 9-12, wherein the compound of PGG extracted from *Paeonia lactiflora* Pall. is further extracted via a methanol, and separated by a medium-pressure liquid chromatography (MPLC) and a Sephadex LH-20 column respectively with the following conditions: in the MPLC, using a dichloromethane and a second methanol as solvents in a mobile phase with concentration gradient conditions: 100% dichloromethane to 60% dichloromethane/40% methanol for 1 hour, 60% dichloromethane and 40% methanol to 100% methanol for 20 minutes and then 100% methanol for 20 minutes, and in the Sephadex LH-20 column, using a third methanol as a solvent in a mobile phase with flow rate: 18 mL/minute.
14. The method of any one of Embodiments 9-13, wherein the compound of PGG extracted from Galla Chinesis is further extracted via a methanol, and separated by a medium-pressure liquid chromatography (MPLC) and a Sephadex LH-20 column respectively with the following conditions: in the MPLC, an E1 fraction washed-out by dichloromethane:methanol=90:10, an E2 fraction washed-out by ethyl acetate:methanol:0.1% acetic acid=15:2:0.5, an E3 fraction washed-out by 100% methanol, and in the Sephadex LH-20 column, using a second methanol as a mobile phase.
15. The method of any one of Embodiments 9-14, wherein the PGG interferes with a stability of a c-Myc protein in vivo.
16. A method for evaluating a therapeutic effect of a medicament in treating a liver tumor, comprising the steps of: (a) providing a Huh7 Glycine N-methyltransferase (GNMT) promoter-luciferase (H7GPL) cell model for the liver tumor; (b) administering to the Huh7 Glycine N-methyltransferase (GNMT) promoter-luciferase (H7GPL) cell model the medicament to be tested for the therapeutic effect; and (c)

determining whether the medicament is effective for treating the liver tumor based on a GNMT promoter-driven luciferase reporter assay.

17. The method of Embodiment 16, wherein *Paeonia lactiflora* Pall. is selected as the medicament when a Z score corresponding to the GNMT promoter-driven luciferase reporter assay is greater than 1.5.

18. The method of any one of Embodiments 16-17, wherein *Paeonia lactiflora* Pall. is extracted via first a methanol, and separated by a medium-pressure liquid chromatography (MPLC) and a Sephadex LH-20 column respectively with the following conditions: in the MPLC, using a dichloromethane and a second methanol as solvents in a mobile phase with concentration gradient conditions: 100% dichloromethane to 60% dichloromethane/40% methanol for 1 hour, 60% dichloromethane and 40% methanol to 100% methanol for 20 minutes and then 100% methanol for 20 minutes, and in the Sephadex LH-20 column, using a third methanol as a solvent in a mobile phase with flow rate: 18 mL/minute.

19. The method of any one of Embodiments 16-18, wherein Galla Chinesis is selected as the medicament when a Z score corresponding to the GNMT promoter-driven luciferase reporter assay is greater than 1.5.

20. The method of any one of Embodiments 16-19, wherein Galla Chinesis is extracted via a first methanol, and separated by a medium-pressure liquid chromatography (MPLC) and a Sephadex LH-20 column respectively with the following conditions: in the MPLC, an E1 fraction washed-out by dichloromethane:methanol=90:10, an E2 fraction washed-out by ethyl acetate:methanol:0.1% acetic acid=15:2:0.5, an E3 fraction washed-out by 100% methanol, and in the Sephadex LH-20 column, using a second methanol as a mobile phase.

While the invention has been described in terms of what is presently considered to be the most practical and preferred embodiments, it is to be understood that the invention need not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method of manufacturing a pharmaceutical composition for a treatment of a liver cancer, a prostate cancer or a human promyelocytic leukemia, comprising the steps of:
   providing an extract including a compound of 1,2,3,4,6-penta-O-galloyl-Beta-D-glucopyranoside (PGG), wherein the extract is extracted from Galla Chinesis via methanol;
   separating the compound of PGG by a medium-pressure liquid chromatography (MPLC), wherein an E1 fraction is washed-out by dichloromethane:methanol=90:10, an E2 fraction is washed-out by ethyl acetate:methanol:0.1% acetic acid=15:2:0.5, and an E3 fraction is washed-out by 100% methanol, and the fractions E1-E3 are assayed by silica TLC via using a mixture of ethyl acetate:methanl:0.1% acetic acid=15:2:0.5 as the mobile phase to obtain a first active fraction;
   separating and purifying the first active fraction by a Sephadex LH-20 column, via using methanol as the mobile phase to obtain a second active fraction; and
   performing a UPLC analysis on the second active fraction.

* * * * *